United States Patent
Mikoshiba et al.

(10) Patent No.: US 6,465,211 B1
(45) Date of Patent: Oct. 15, 2002

(54) NUCLEIC ACIDS, VECTORS AND TRANSFORMED CELLS FOR MAKING AND USING HIGH AFFINITY IP-3 BINDING POLYPEPTIDES

(75) Inventors: Katsuhiko Mikoshiba, 2-19-25, Inokashira, Mitaka-shi Tokyo, 181-0001 (JP); Teiichi Furuichi, Chiba (JP); Fumio Yoshikawa, Kanagawa (JP); Tsuyoshi Uchiyama, Tokyo (JP)

(73) Assignees: Riken, Saitama (JP); Katsuhiko Mikoshiba, Tokyo (JP)

( * ) Notice: Subject to any disclaimer, the term of this patent is extended or adjusted under 35 U.S.C. 154(b) by 0 days.

(21) Appl. No.: 09/385,222

(22) Filed: Aug. 26, 1999

(30) Foreign Application Priority Data

Aug. 27, 1998 (JP) .......................................... 10-242207

(51) Int. Cl.[7] .......................... C07H 21/00; C12N 15/62; C12N 15/12; C12N 15/67
(52) U.S. Cl. .............. 435/69.1; 435/252.3; 435/252.33; 435/320.1; 435/325; 536/23.1; 536/23.5; 536/23.4
(58) Field of Search .......................... 514/44; 435/320.1, 435/328, 69.1, 252.33, 252.3, 325; 536/23.5, 23.1, 23.4

(56) References Cited

FOREIGN PATENT DOCUMENTS

| | | |
|---|---|---|
| JP | 08245698 | 9/1996 |
| WO | WO 96/00586 | 1/1996 |
| WO | WO96/24846 | * 8/1996 ................. 435/7.5 |

OTHER PUBLICATIONS

Crystal R., "Transfer of genes to humans: Early lessons and obstacles to success." Science, vol. 270: 404–410, 1995.*
Deonarain M., "Ligand–targeted receptor–mediated vectors for gene delivery." Exp. Opin. Ther. Patents, vol. 8 (1): 53–69, 1998.*
Eck et al., "Gene–based therapy." Goodman & Gilman's The Pharmacological Basis of Therapeutics– Ninth Edition, McGraw–Hill: 77–101, 1996.*
Verma et al., "Gene therapy—promises, problems, and prospects". Nature, vol. 389: 239–242, Sep. 1997.*
Miller et al., "Targeted vectors for gene therapy." FASEB Journal, vol. 9: 190–199, Feb. 1995.*
Blau et al., "Molecular Medicine, Gene therapy—A Novel Form of Drug Delivery". The New England Journal of Medicine, vol. 333 (18): 1204–1207, Nov. 1995.*
Anderson FW, "Human gene therapy". Nature, vol. 392 (SUPP): 25–30, Apr. 1998.*
Frommel et al., "An estimate on the effect of point mutation and natural selection on the rate of amino acid replacement in proteins". Journal of Molecular Evolution, vol. 21: 233–257, 1985.*

(List continued on next page.)

Primary Examiner—Scott D. Priebe
(74) Attorney, Agent, or Firm—Fish & Richardson P.C.

(57) ABSTRACT

The present invention provides a high affinity polypeptide having a binding activity to inositol 1,4,5-trisphosphate, to a gene encoding the polypeptide, to a recombinant vector including the gene, to a transformant including the vector and to a method for producing the high affinity polypeptide having a binding activity to inositol 1,4,5-trisphosphate.

22 Claims, 9 Drawing Sheets

OTHER PUBLICATIONS

Ngo et al., "Computational Complexity, protein structure prediction, and the Levinthal Paradox". The protein folding problem and tertiary structure prediction: 492–495, 1994.*

Bowie et al., "Deciphering the message in protein sequences: tolerance to amino acid substitutions". Science, vol. 247: 1306–1310, Mar. 1990.*

Harnick et al., "The Human Type I Inositol 1, 4, 5–trisphosphate Receptor from T Lymphocytes". Journal of Biol. Chem., vol. 270 (6): 2833–2840, Feb. 1995.*

Furuichi et al., "Nucleotide Sequence of cDNA encoding P400 protein in the mouse cerebellum". Nucleic Acid Res., vol. 17 (13): 5385–5386, 1989.*

Mignery et al., "Structure and Expression of the Rat Inositol 1, 4, 5–trisphosphate Receptor". Journal of Biol. Chem., vol. 265 (21): 12679–12685, Sep. 1997.*

Yamada et al., "Human Inositol 1, 4, 5–trisphosphate type–1 receptor, InsP3R1: structure, function, regulation of expression and chromosomal localization". Biochem. J., vol. 302: 781–790, 1994.*

Yoshikawa et al.; High Efficient Expression of the Functional Ligand Binding Site of the Inositol 1,4,5–Trisphosphate Receptor in *Escherichia coli*, 1999, Biochemical and Biophysical Research Comm.: 792–797.*

Newton et al.; Co–expression in Vertebrate Tissues and Cell Lines of Multiple Inositol 1,4,5–Trisphosphate (InsP) Receptors with Distinct Affinites for InsP, 1994, The Journal of Biological Chemistry, vol. 269,No. 46:28613–28619.*

Yoshikawa, et al., "Mutational Analysis of the Ligand Binding Site of the Inositol 1,4,5–Trisphosphate Receptor", The Journal of Biological Chemistry, vol. 271, No. 30, pp. 18277–18284, Jul. 26, 1996.

Furuichi et al., *Nature*, 342:32–38, Nov. 2, 1989 (XP–002141737).

* cited by examiner

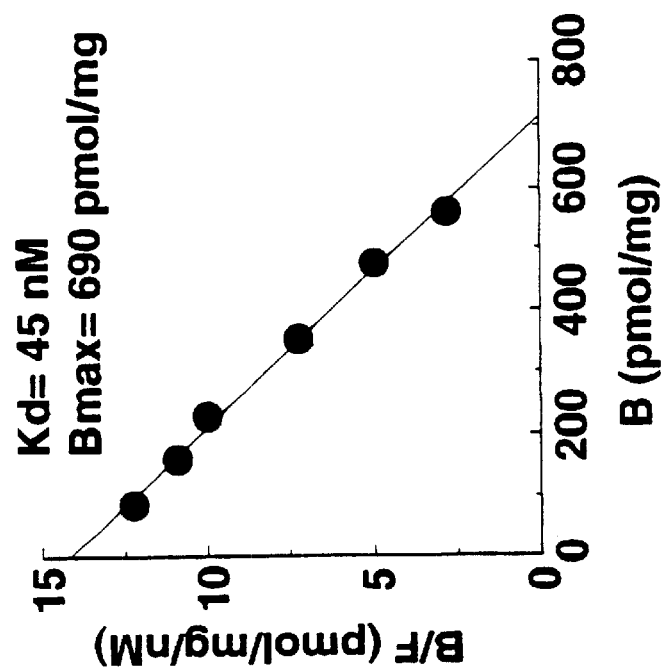
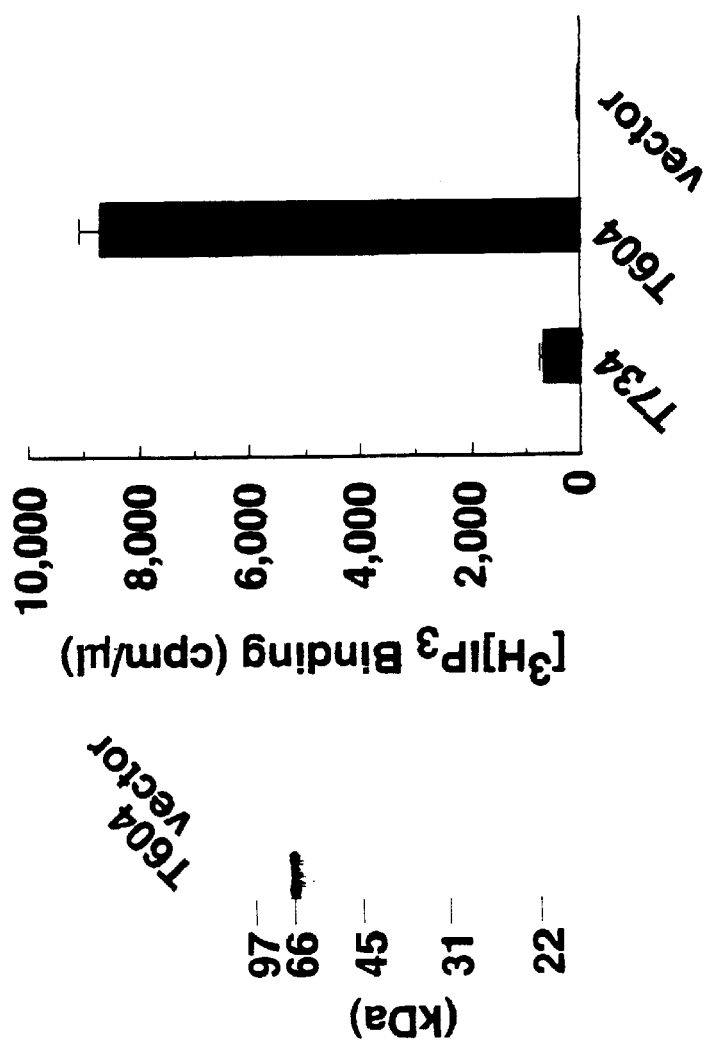
FIG. 2A
FIG. 2B
FIG. 2C

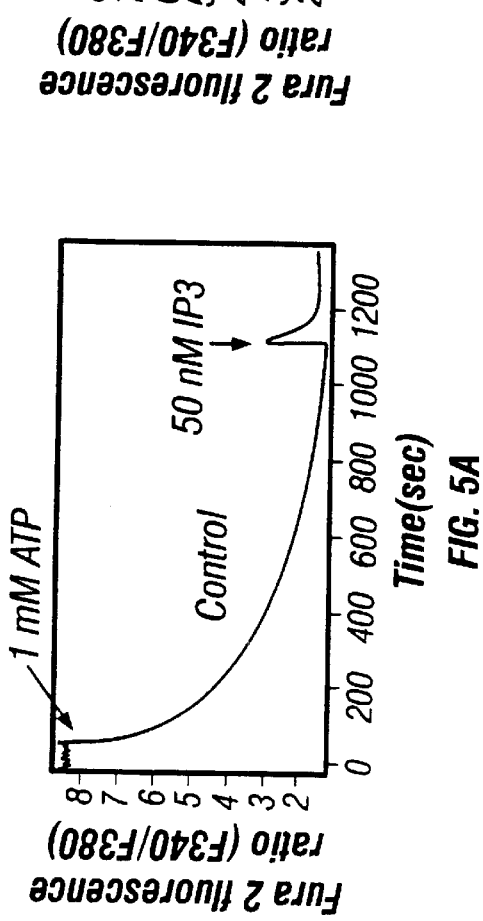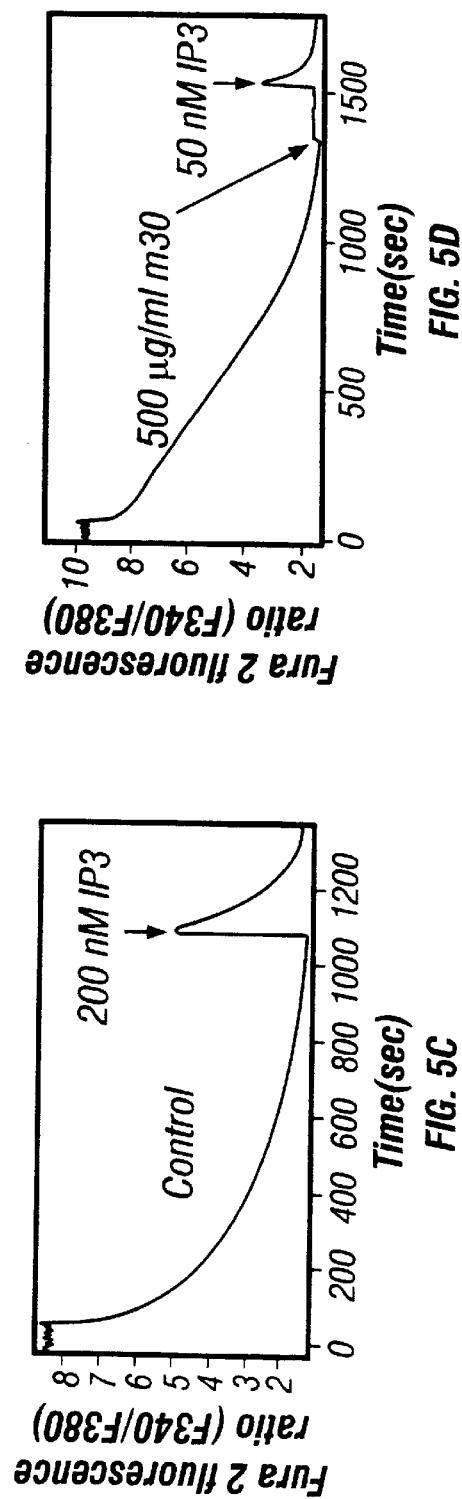
FIG. 5A
FIG. 5B
FIG. 5C
FIG. 5D

NUCLEIC ACIDS, VECTORS AND TRANSFORMED CELLS FOR MAKING AND USING HIGH AFFINITY IP-3 BINDING POLYPEPTIDES

The present application under 35 USC §119 claims the benefit of a foreign priority application filed in Japan, serial number 242207/1998, filed Aug. 27, 1998.

FIELD OF THE INVENTION

The present invention relates to a high affinity polypeptide having a binding activity to inositol 1,4,5-trisphosphate, to a gene encoding the polypeptide, to a recombinant vector including the gene, to a transformant including the vector and to a method for producing the high affinity polypeptide having a binding activity to inositol 1,4,5-trisphosphate.

BACKGROUND OF THE INVENTION

Inositol 1,4,5-trisphosphate (hereinafter, also referred to as "$IP_3$") is one of second messengers which are produced by inositol phospholipid metabolism activated in response to an extracellular stimului such as hormones, growth factors, neurotransmitters or the like. $IP_3$ is a substance that induces the increase of intracellular calcium concentration. The $IP_3$-induced calcium increase is a crucial and highly universal signal transmission mechanism that is involved in many cell functions in a wide variety of animals. For example, $IP_3$ controls many physiological functions such as fertilization, blastogenesis, development and differentiation, cell growth, secretion, immune system, muscle contraction, and cranial nerve functions (gustation, vision, memory, learning, etc.) in diverse organisms, for example, invertebrate such as nematoda (nemathelminthes), Drosophila (arthropoda) and cuttlefish (mollusca), and vertebrata such as mouse and human.

On the molecular level, this mechanism is initiated by the binding between an $IP_3$ and its target, an $IP_3$ receptor. Specifically, when the $IP_3$ binds to the $IP_3$ receptor (a calcium channel susceptible to $IP_3$) present in an intracellular calcium-storing site (endoplasmic reticulum, etc.), the channel opens and releases calcium from the calcium-storing site into the cytoplasm, thereby controlling the activities of calcium-dependent proteins and enzymes.

Heparin, adenophostin (a kind of fungal metabolite) and Xestospongin (a kind of sponge metablite) are examples of substances that might affect the signal transmission by the $IP_3$-induced calcium. However, although heparin inhibits the binding between the $IP_3$ and the $IP_3$ receptor, its specificity is low since there are various targets in the cell. Adenophostin is an antagonistic agonist of the binding between the $IP_3$ and the $IP_3$ receptor, and is a powerful activator of the $IP_3$ receptor channel. However, its use is limited since its yield from fungus is low and it cannot transport across the membrane. Xestospongin has recently been reported as an inhibitor of the $IP_3$ receptor channel that does not influence the binding of $IP_3$. Again, its yield is low and there are still questions remaining as to its specificity. Thus, currently, there is almost no substance that is considered to effectively act on $IP_3$-induced calcium signal transmission. In particular, there has been no substance or system that inhibits $IP_3$-induced calcium signal transmission by specifically trapping $IP_3$ that has increased on the cell level.

SUMMARY OF THE INVENTION

The present invention provides a high affinity polypeptide having a binding activity to inositol 1,4,5-trisphosphate, a gene encoding the polypeptide, a recombinant vector containing the gene, a transformant containing the vector and a method for producing the high affinity polypeptide having a binding activity to inositol 1,4,5-trisphosphate.

In order to solve the above-described problem, the present inventors have gone through intensive studies and have succeeded in isolating a high affinity polypeptide having an extremely high binding activity to $IP_3$ from a protein including a part of the N-terminal amino acid region of an $IP_3$ receptor.

The present invention provides a recombinant polypeptide of the following (a), (b) or (c):

(a) a polypeptide comprising an amino acid sequence shown in SEQ ID NO: 2;

(b) a polypeptide comprising an amino acid sequence having deletion, substitution or addition of at least one amino acid in the amino acid sequence shown in SEQ ID NO: 2, and having a high affinity binding activity to inositol 1,4,5-trisphosphate; or (c) a polypeptide having at least 70% homology with the amino acid sequence shown in SEQ ID NO: 2, and having a high affinity binding activity with inositol 1,4,5-trisphosphate.

The present invention also provides a gene coding for a polypeptide of the above (a), (b) or (c); or a gene coding for a polypeptide having at least 70% homology with the gene and having a high affinity binding activity with inositol 1,4,5-trisphosphate.

The present invention further provides a gene comprising DNA of the following (d) or (e):

(d) DNA of a nucleotide sequence shown in SEQ ID NO: 1; or (e) DNA of a nucleotide sequence having at least 70% homology with the DNA of the nucleotide sequence shown in SEQ ID NO: 1, and coding for a polypeptide having a high affinity binding activity with inositol 1,4,5-trisphosphate.

The present invention provides a recombinant vector comprising any one of the above-described genes.

The present invention also provides a transformant comprising the above recombinant vector.

The present invention further provides a method for producing any one of the above-mentioned polypeptides, the method comprising: culturing the above-mentioned transformant; and collecting, from the obtained culture, a polypeptide having a high affinity binding activity to inositol 1,4,5-trisphosphate.

This and other advantages of the present invention will become apparent to those skilled in the art upon reading and understanding the following detailed description with reference to the accompanying figures.

This specification includes part or all of the contents as disclosed in the specification and/or drawings of Japanese Patent Application No. 10-242207 which is a priority document of the present invention.

BRIEF DESCRIPTION OF THE DRAWINGS

FIGS. 2A–2C show high expression and $IP_3$-binding activity of T604;

FIGS. 5A–5F are graphs showing the effects of low-affinity G224-m30 and GST on $IP_3$-induced $Ca^{2+}$ release;

DESCRIPTION OF THE PREFERRED EMBODIMENTS

Figure 1:
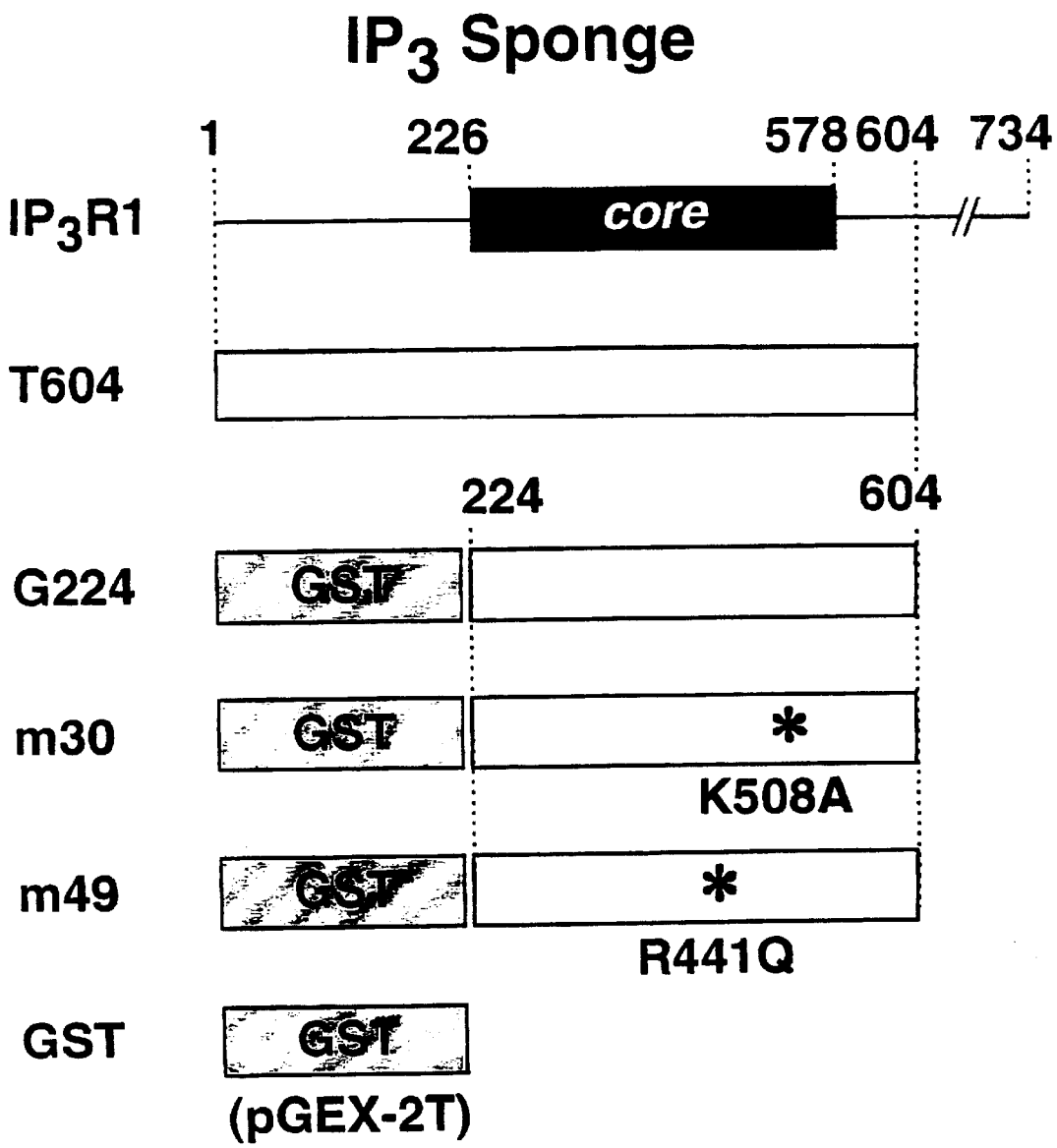
FIG. 1 shows the structures of $IP_3$ sponges.

Hereinafter, the present invention will be described in more detail.

A polypeptide of the present invention specifically binds to IP$_3$ with a very high affinity, and includes a part (a cut) of N-terminal amino acid region of the natural IP$_3$ receptor (thus also referred to as a cut-type polypeptide) The polypeptide of the invention is often referred to as a high affinity IP$_3$-binding polypeptide.

1. Cloning a Gene Coding for the IP$_3$ Receptor

In order to obtain a high affinity IP$_3$-binding polypeptide of the invention, a gene encoding the natural IP$_3$ receptor protein is cloned. The nucleotide sequence of the IP$_3$ receptor gene is already known (*Nucleic Acid Res.* 17:5385–5386, 1989; *Nature* 342:32–38, 1989). The gene may, for example, be prepared according to the following gene engineering procedure.

(i) Preparation and Screening of cDNA Library Encoding the IP$_3$ Receptor

A known procedure may be employed to prepare mRNA of the IP$_3$ receptor. For example, total RNA is obtained by treating a tissue or a cell from a mouse brain with a guanidine reagent, a phenol reagent or the like. Then, poly(A)+RNA(mRNA) is obtained according to an affinity column method or a batch method using poly (U) sepharose, etc. By using the obtained mRNA as a template as well as oligo dT primer and reverse transcriptase, a single-stranded cDNA is synthesized. Based on the single-stranded cDNA, a double-stranded cDNA is synthesized and introduced into a suitable cloning vector to prepare a recombinant vector to transform *E.coli* or the like. The transformant is selected based on indices such as tetracycline and ampicillin resistance, thereby obtaining a cDNA library.

The transformation of *E.coli* may be conducted according to the method of Hanahan [Hanahan, D., *J. Mol. Biol.* 166:557–580 (1983)]. Specifically, the recombinant vector is added to a prepared competent cell under the presence of calcium chloride, magnesium chloride or rubidium chloride. When a plasmid is used as the vector, it should contain a gene resistant to drugs such as tetracycline and ampicillin. Besides plasmids, a cloning vector such as λ phage may also be used.

The thus-obtained transformant is screened for strains with the DNA of interest by, for example, "expression cloning" through immunoscreening using an antibody, or by polymerase chain reaction (PCR) using a primer synthesized from a known sequence.

The thus-obtained DNA fragment or DNA amplified fragment coding for the antibody epitope is labeled with $^{32}$p, $^{35}$S, biotin or the like to be used as a probe for hybridizing with the transformant DNA denatured and bound on a nitrocellrose filter. Then, the obtained positive strains may be screened for the target DNA fragment.

(ii) Determination of the Nucleotide Sequence

The obtained clone is determined for its nucleotide sequence. The nucleotide sequence may be determined according to a known method such as Maxam-Gilbert chemical modification method, dideoxynucleotide chain termination method using M13 phage. Generally, the sequence is determined using an automatic DNA sequencer (e.g., Perkin-Elmer 373A DNA sequencer).

The nucleotide sequence of the natural (full-length) gene coding for the IP$_3$ receptor and the full-length amino acid sequence of the IP$_3$ receptor are shown in SEQ ID NOS. 3 and 4, respectively.

2. Design and Synthesis of a Gene Coding for a High Affinity IP$_3$-binding Polypeptide of the Invention (i) Design and Synthesis of a Gene Coding for a High Affinity IP$_3$-binding Polypeptide A high affinity IP$_3$-binding polypeptide of the invention includes a cut of N-terminal amino acid region, that is, Amino acids 579 to at least 800, preferably Amino acids 579 to at least 734, of the amino acid sequence of the full-length IP$_3$ receptor protein (SEQ ID NO:4). According to the present invention, this cut-type polypeptide is also referred to as an IP$_3$ sponge (FIG. 1). Due to this cut, the polypeptide (IP$_3$ sponge) of the invention gains a very strong specific binding ability to IP$_3$ (high affinity IP$_3$-binding activity).

Herein, the phrase "high affinity" is used in the situation where the IP$_3$ sponge has an IP$_3$ affinity that is about 100 to 1,000 times (preferably 500 to 1,000 times) higher than that of the natural IP$_3$ receptor.

According to the present invention, the IP$_3$ sponge also includes at least the amino acid sequence shown in SEQ ID NO: 14, which corresponds to Amino acids 226–578 of the amino acid sequence of SEQ ID NO: 4. Herein, this region is referred to as a "core" region.

Based on the above-described facts, the length of the fragment of the invention and the length of the DNA coding for the fragment can be determined at ones discretion providing that the high affinity IP$_3$-binding activity is maintained. The fragment may include, for example, Amino acids 224–604 of the amino acid sequence of SEQ ID NO: 4 (encoded by Nucleotides 998–2140 of the nucleotide sequence of SEQ ID NO: 3); Amino acids 1–604 of the amino acid sequence of SEQ ID NO: 4 (encoded by Nucleotides 329–2140 of the nucleotide sequence of SEQ ID NO: 3); or Amino acids 1–734 of the amino acid sequence of SEQ ID NO: 4 (encoded by Nucleotides 329–2540 of the nucleotide sequence of SEQ ID NO: 3).

These fragments are obtained through PCR using primers that are designed based on nucleotide regions of the nucleotides shown in SEQ ID NO. 3 outside the regions of the respective fragments, as well as the DNA coding for the natural IP$_3$ receptor (SEQ ID NO: 3, *Nucleic Acid Res.* 17:5385–5386, 1989; *Nature* 342: 32–38, 1989) as a template.

(ii) Preparation of a Gene Encoding a Mutant-type IP$_3$ Sponge of the Invention (Mutant-type IP$_3$ Gene)

According to the present invention, the amino acid sequence of the IP$_3$ sponge may, at least partially, be introduced with a mutation. Such a mutant-type IP$_3$ sponge is also contemplated as the IP$_3$ sponge of the present invention. A mutation is introduced into the amino acid sequence, by mutating the nucleotide sequence of the gene coding for the amino acid sequence of the IP$_3$ sponge.

The mutation is introduced into the gene according to a known method such as Kunkel method, Gapped duplex method or any method equivalent thereof. For example, site-directed mutagenesis may be employed in which a mutant oligonucleotide is used as a primer (Yoshikawa, F. et al., *J. Biol. Chem.* 271: 18277–18284, 1996). Alternatively, a mutation may be introduced by using a mutagenesis kit such as Mutant-K (Takara), Mutant-G (Takara) and a series of LA PCR in vitro Mutagenesis kits (Takara).

First, based on the nucleotides of the gene coding for the IP$_3$ sponge of the invention (also referred to as an "IP$_3$ sponge gene"), a primer is synthesized such that the primer includes a mutated nucleotide or site and about 10 nucleotides flanking the mutated nucleotide or site. Using this primer as well as the $IP_3$ sponge gene as a template, PCR reaction is conducted. The resultant is purified and then treated with a suitable restriction enzyme, thereby obtaining the mutant-type $IP_3$ sponge gene of interest.

(iii) Determination of the Nucleotide Sequences

The nucleotide sequence of the genes obtained through (i) and (ii) is determined. The determination is conducted by a known method such as Maxam-Gilbert chemical modification method, dideoxynucleotide chain termination method using M13 phage, or any other method. Generally, an automatic sequencer (e.g., 373A DNA sequencer produced by Perkin-Elmer) is used.

A nucleotide sequence of an $IP_3$ sponge gene of the invention and an amino acid sequence of the $IP_3$ sponge of the invention are shown in SEQ ID NOS: 1 and 2, respectively. The polypeptide of this amino acid sequence may include at least one deletion, substitution, addition or the like as long as it has a high affinity with $IP_3$ and has an activity of specifically binding to $IP_3$.

For example, at least one, preferably about 1 to 10, more preferably 1 to 5 of the amino acids in the core region (the amino acid sequence shown in SEQ ID NO: 2) may be deleted; at least one, preferably about 1 to 10, more preferably 1 to 5 amino acids may be added to the amino acid sequence of the core region; or at least one, preferably 1 to 10, more preferably 1 to 5 of the amino acids in the core region may be replaced with other amino acids.

The polypeptide of the present invention is not limited by the length of the amino acid sequence as long as the amino acid sequence contains the amino acid sequence of the core region and a cut of N-terminal Amino acids 579 to at least 800, preferably N-terminal Amino acids 579 to at least 734 of the natural-type $IP_3$ receptor (SEQ ID NO:4). For example, Amino acids 224–604 (polypeptide "G224") of the amino acid sequence shown in SEQ ID NO:4, and the gene encoding G224, are also contemplated as the $IP_3$ sponge and the $IP_3$ sponge gene of the invention, respectively.

The polypeptide G224 may have a mutation of at least one, preferably about 1 to 10, more preferably 1 to 5 amino acids. Thus, the $IP_3$ sponge of the invention may include an amino acid sequence where lysine at Position 508 of the amino acid sequence G224 is replaced with alanine (mutation "m30") or where arginine at Position 441 of the amino acid sequence G224 is replaced with glutamine (mutation "m49") (FIG. 1). Herein, the numbers indicating the positions of the amino acids are based on the amino acid sequence shown in SEQ ID NO:4 (e.g., Position 1 is the first amino acid of SEQ ID NO: 4).

A polypeptide including an amino acid sequence having 70% or more homology with the core region (SEQ ID NO: 2), and having a high affinity binding activity with inositol 1,4,5-trisphosphate is also contemplated as the present invention.

Also contemplated as the present invention is a gene coding for the polypeptide having the above-described mutation in its amino acid sequence, and having a high affinity binding activity with $IP_3$ receptor. In addition, a nucleotide sequence coding for the amino acids included in the $IP_3$ sponge of the present invention, and a degenerate isomer coding for the same polypeptide with different degenerate codons are also contemplated as the genes of the invention. Also contemplated as the present invention is DNA having at least 70% homology with the nucleotide sequence of these genes, for example, DNA of other type belonging to the $IP_3$ receptor gene family that codes for a region corresponding to the polypeptide of the present invention.

Once the nucleotide sequence of the gene of the present invention is determined, the gene may be obtained by PCR using a primer that is synthesized chemically or that is synthesized from the determined nucleotide sequence.

3. Preparation of Recombinant Vector and Transformant Containing $IP_3$ Sponge Gene of the Invention (i) Preparation of Recombinant Vector A recombinant vector of the invention may be obtained by ligating (inserting) the $IP_3$ sponge gene of the invention to (into) a suitable vector. The vector for inserting the gene of the invention is not limited to a specific one as long as it is replicable in a host cell. Examples of such vector include but not limited to plasmid DNA and phage DNA.

The plasmid DNA is, for example, plasmid from *E.coli* (e.g., pET-3a, pBR322, pBR325, pUC118, pUC119, etc.), plasmid from bacillus (e.g., pUB110, pTP5, etc.), or plasmid from yeast (e.g., YEp13, YEp24, YCp50, etc.). The phage DNA is, for example, λ phage. Similarly, an animal virus vector such as retrovirus, adenovirus or vaccinia virus vectors, or an insect virus vector such as a baculovirus vector may also be used. A fusion plasmid in which GST, GFP, His-tag, Myc-tag or the like is linked with each other may also be used (e.g., pGEX-2T, pEGFP-N3).

To insert the gene of the invention into the vector, first, the purified DNA is cleaved with suitable restriction enzymes. Then, the cleaved fragment is inserted into a restriction site or a multicloning site of the suitable vector DNA.

The gene of the present invention should be integrated into the vector such that the gene can function. If desired, the vector of the invention may include, other than the gene of the invention and the promoter, for example, a cis-element (e.g., an enhancer), a splicing signal, a poly(A) tail signal, a selective marker, and a ribosome binding sequence (SD sequence). Examples of the selective marker include a dihydrofolate reductase gene, an ampicillin-resistant gene and a neomycin-resistant gene.

(ii) Preparation of Transformant

A transformant of the invention may be obtained by introducing the recombinant vector of the invention into a host cell in such a manner that the gene of interest is capable to be expressed. The host cell is not limited to a specific one as long as it can express the gene of the present invention. Bacteria such as genus Escherichia (e.g., *Escherichia coli*), genus Bacillus (e.g., *Bacillus subtilis*), genus Pseudomonas (e.g., . *Pseudomonas putida*), yeast such as *Saccharomyces cerevisiae* and *Schizosaccharomyces pombe*, animal cells (e.g., COS, CHO, HEK293, PC12 cells), and insect cells (e.g., Sf9 and Sf21) are exemplified.

When a bacterium such as *E.coli* is used as the host, it is preferable that the recombinant vector of the present invention is capable of autonomous replication in the host and that it includes a promoter, a ribosome binding sequence, the gene of the invention and a transcription termination sequence. The recombinant vector may also include a gene for controlling the promoter.

As the *E.coli*, *E.coli* BL21, JM109 and HB101 are exemplified and as bacillus, *Bacillus subtilis* MI 114 and 207-21 are exemplified.

Any promoter may be used as long as it can be expressed in a host cell like *E.coli*. For example, a promoter derived from *E.coli* or phage, e.g., trp promoter, lac promoter, $p_L$ promoter or PR promoter, may be used. Artificially designed and modified promoter like tac promoter may also be used.

The recombinant vector may be introduced into the host bacterium according to any method for introducing DNA into a bacterium. For example, calcium ion method (Cohen, S. N. et al., *Proc. Natl. Acad. Sci., USA*, 69: 2110–2114 (1972)) and an electroporation method may be employed.

An yeast such as *Saccharomyces cerevisiae, Schizosaccharomyces pombe* or *Pichia pastoris* may also be used as the host. In this case, the promoter may be any promoter that can be expressed in the yeast. Examples of such promoter include but not limited to gal1 promoter, gal10 promoter, heat shock protein promoter, MF 1 promoter, PHO5 promoter, PGK promoter, GAP promoter, ADH promoter and AOX1 promoter.

The recombinant vector may be introduced into the yeast by any method for introducing DNA into an yeast. For example, electroporation method (Becker, D. M. et al., *Methods Enzymol.*, 194, 182–187 (1990)), spheroplast method (Hinnen, A. et al., *Proc. Natl. Acad. Sci., USA*, 75, 1929–1933 (1978)), or lithium acetate method (Itoh, H., *J. Bacteriol.*, 153, 163–168 (1983)) may be employed.

An animal cell such as simian cell (e.g., COS-7, Vero), Chinese hamster ovary cell (CHO cell), mouse L cell, rat cell (e.g., GH3, PC12 or NG108-15) or human cell (e.g., FL, HEK293, HeLa or Jurkat) may also be used as the host. As a promoter, for example, SR promoter, SV40 promoter, LTR promoter or β-actin promoter may be used. Other than these promoters, an early gene promoter of human cytomegalovirus may also be used.

The recombinant vector may be introduced into the animal cell, for example, by an electroporation method, a calcium phosphate method or a lipofection method.

An insect cell such as Sf9 cell, Sf21 cell or the like may also be used as the host. The recombinant vector may be introduced into the insect cell, for example, by a calcium phosphate method, a lipofection method or an electroporation method.

4. Production of $IP_3$ Sponge

The $IP_3$ sponge of the present invention may be obtained by culturing the above-described transformant, and recovering the $IP_3$ sponge from the culture product. The term "culture" as used herein refers to a culture supernatant, a cultured cell or microbial cell, or a cell or microbial cell debris.

The transformant of the invention is cultured according to a general method employed for culturing the host.

A medium for culturing the transformant obtained from a microorganism host such as *E.coli* or yeast may be either a natural or a synthetic medium providing that it contains carbon sources, nitrogen sources, inorganic salts and the like assimilable by the microorganism, and that it can efficiently culture the transformant.

As carbon sources, carbohydrate such as glucose, fructose, sucrose, starch; organic acids such as acetic acid, propionic acid; and alcohols such as ethanol and propanol may be used.

As nitrogen sources, ammonia; ammonium salts of inorganic or organic acids such as ammonium chloride, ammonium sulfate, ammonium acetate and ammonium phosphate; other nitrogen-containing compounds; Peptone; meat extract; corn steep liquor and the like may be used.

As inorganic substances, potassium dihydrogen phosphate, dipotassium hydrogen phosphate, magnesium phosphate, magnesium sulfate, sodium chloride, iron(II) sulfate, manganese sulfate, copper sulfate, calcium carbonate and the like may be used.

The cultivation is generally performed under aerobic conditions such as shaking or aeration agitating conditions at 37° C. for 6 to 24 hours. During the cultivation, pH is maintained at 7.0 to 7.5. pH is regulated with an inorganic or organic acid, an alkali solution or the like. If necessary, an antibiotic such as ampicillin, tetracycline or the like may be added to the medium during the cultivation.

When culturing a microorganism transformed with an expression vector using an inducible promoter, an inducer may be added to the medium at need. For example, isopropyl 1-thio-β-D-galactoside (IPTG) may be added to the medium when culturing a microorganism transformed with an expression vector pET-3a having T7 promoter (that is inducible with IPTG). When culturing a microorganism transformed with an expression vector using trp promoter (that is inducible with indole acetic acid (IAA)), IAA may be added to the medium.

A transformant obtained with an animal cell host may be cultured in a generally used medium such as RPMI1640 medium or DMEM medium, or a medium obtained by supplementing the generally used medium with fetal bovine serum and the like.

The cultivation is generally conducted under 5% $CO_2$ at 37° C. for 1 to 30 days. If necessary, an antibiotic such as kanamycin, penicillin or the like may be added to the medium during the cultivation.

After the cultivation, in the case where a microbial cell or a cell intracelluraly produced the $IP_3$ sponge of the invention, the $IP_3$ sponge is collected by disrupting the microbial cell or the cell by sonication, freezing and thawing method, or homogenizing. In the case where a microbial cell or a cell extracellularly produced the $IP_3$ sponge of the invention, the microbial cell or the cell is removed from the culture through centrifugation or the like before, or the culture solution is directly subjected to the isolation/purification procedure. The $IP_3$ sponge of the invention is isolated and purified from the culture through a general biochemical method for isolating and purifying a protein, such as ammonium sulfate precipitation, gel chromatography, ion exchange chromatography, affinity chromatography, or a combination thereof.

5. Therapeutic Agent and Agent for Gene Therapy

Since the protein and the gene of the invention has $IP_3$ neutralizing activity, they are useful as an antagonist for $IP_3$-induced calcium, a therapeutic agent and an agent for gene therapy for diseases associated with calcium production. The therapeutic agent or the agent for gene therapy of the invention can be administered orally or parenterally and systemically or locally.

When the protein or the gene of the invention is used as a therapeutic agent or an agent for gene therapy for disease associated with calcium production, the disease to be treated is not particularly limited. For example, the protein or the gene may be used for diseases in the nervous system, blood vascular system, respiratory system, digestive system, lymphatic system, urinary system, reproduction system or the like for the specific purpose of treatment or prevention. These diseases may be in the form of a single disease or may be complicated by one of these diseases or by some disease other than those mentioned above; any of such forms may be treated with the protein or the gene of the invention.

When the therapeutic agent of the invention is administered orally, the agent may be formulated into a tablet, capsule, granule, powder, pill, troche, internal liquid agent, suspension, emulsion, syrup or the like. Alternatively, the therapeutic agent may be prepared into a dry product which is re-dissolved just before use. When the therapeutic agent of the invention is administered parenterally, the agent may be formulated into a intravenous injection (including drops), intramuscular injection, intraperitoneal injection, subcutaneous injection, suppository, or the like. Injections are supplied in the form of unit dosage ampules or multi-dosage containers.

These formulations may be prepared by conventional methods using appropriate excipients, fillers, binders, wetting agents, disintegrating agents, lubricating agents, surfactants, dispersants, buffers, preservatives, dissolution aids, antiseptics, flavoring/perfuming agents, analgesics, stabilizers, isotonicity inducing agents, etc. conventionally used in pharmaceutical preparations.

Each of the above-described formulations may contain pharmaceutically acceptable carriers or additives. Specific examples of such carriers or additives include water, pharmaceutically acceptable organic solvents, collagen, polyvinyl alcohol, polyvinylpyrrolidone, carboxyvinyl polymers, sodium alginate, water-soluble dextran, sodium carboxymethyl amylose, pectin, xanthan gum, gum arabic, casein, gelatin, agar, glycerol, propylene glycol, polyethylene glycol, vaseline, paraffin, stearyl alcohol, stearic acid, human serum albumin, mannitol, sorbitol and lactose. One or a plurality of these additives are selected or combined appropriately depending of the form of the preparation.

The dosage levels of the therapeutic agent of the invention will vary depending on the age of the subject, the route of administration and the number of times of administration and may be varied in a wide range. When an effective amount of the protein of the invention is administered in combination with an appropriate diluent and a pharmaceutically acceptable carrier, the effective amount of the protein can be in the range from 0.0001 to 1000 mg/kg per administration. The therapeutic agent is administered once a day or in several dosages per day for at least one day.

When the gene of the invention is used as an agent for gene therapy for diseases associated with calcium production, the gene of the invention may be directly administered by injection. Alternatively, a vector incorporating the gene of the invention may be administered. Specific examples of a suitable vector for this purpose include an adenovirus vector, adeno-associated virus vector, herpes virus vector, vaccinia virus vector and retrovirus vector. The gene of the invention can be administered efficiently by using such a virus vector. Alternatively, the gene of the invention may be enclosed in phospholipid vesicles such as liposomes, and the resultant liposomes may be administered to the subject. Briefly, since liposomes are biodegradable material-containing closed vesicles, the gene of the invention is retained in the internal aqueous layer and the lipid bilayer of liposomes by mixing the gene with the liposomes (a liposome-gene complex). Subsequently, when this complex is cultured with cells, the gene in the complex is taken into the cells (lipofection). Then, the resultant cells may be administered by the methods described below.

As a method for administering the agent for gene therapy of the invention, local administration to tissues of the central nervous system (brain, spiral cord), blood vascular system (artery, vein, heart), respiratory system (trachea, lung), digestive system (salivary glands, stomach, intestines, liver, pancreas), lymphatic system (lymph node, spleen, thymus), urinary system (kidney), reproduction system (testis, ovary, uterus) or the like may be performed in addition to conventional systemic administration such as intravenous or intra-arterial administration. Further, an administration method combined with catheter techniques and surgical operations may also be employed.

The dosage levels of the agent for gene therapy of the invention vary depending on the age, sex and conditions of the subject, the route of administration, the number of times of administration, and the type of the formulation. Usually, it is appropriate to administer the gene of the invention in an amount of 0.01–100 mg/adult body/day.

EXAMPLES

Hereinafter, the present invention will be described in detail by way of examples which do not limit the technical scope of the present invention.

Example 1

Construction of Expression Plasmid for High Affinity $IP_3$-Binding Polypeptide ($IP_3$-Sponge)

The N-terminal amino acids (734 amino acids) (polypeptide T734) of a mouse Type-1 $IP_3$ receptor (m$IP_3$R1) has a specific $IP_3$-binding activity. The cDNA portion coding for polypeptide T734 was cloned into *E.coli* expression vector pET-3a (whose expression is controlled by T7 promoter that is induced upon addition of IPTG) to obtain plasmid pET-T734 (Yoshikawa F. et al., *J. Biol. Chem.* 271:18277–18284, 1996). Using this plasmid (pET-T734) as a parent plasmid, the following expression plasmids were constructed for $IP_3$-binding polypeptides. Herein, an $IP_3$-binding polypeptide with high affinity is also referred to as an "$IP_3$ sponge".

(1-1) Expression plasmid for high affinity $IP_3$ sponge "T604"

A gene coding for polypeptide T604 that corresponds to the first methionine (M-1) to the lysine at Position 604 (K-604) of polypeptide T734 was prepared. Specifically, site-directed mutagenesis was conducted by PCR using a complementary oligonucleotide (Yoshikawa F. et al., *J Biol Chem*, 271:18277–18284, 1996) to introduce a stop codon (TAA) and a subsequent BamHI recognition site (GGATCC) at Position 605 of T734.

```
Sense primer:
                                    (SEQ ID NO: 5)
   5'-TGTCAGACATATGCGTGTTGGAA-3'
           NdeI Antisense primer:
                                    (SEQ ID NO: 6)
   5'-CGCGGGATCCTTATTTCCGGTTGTTGTGGAGCAGGG-3'
       BamHI
```

The sense primer was introduced with a NdeI cleavage recognition sequence (CATATG) (underlined) including the first methionine codon (ATG).

A total of 100 μl PCR reaction solution was used. The PCR reaction solution contained 100 ng template DNA, 10 mM KCl, 6 mM $(NH_4)_2SO_4$, 20 mM Tris-HCl (pH 8.2), 2 mM $Mgcl_2$, 0.1% TritonX-100, 10 μg/ml BSA, 200 μM dNTPs, 1 μM sense primer, 1 μM anti-sense primer and 2.5 unit Pfu DNA polymerase. The PCR reaction was performed at 95° C. for 1 min. and then through 30 cycles of: 95° C. for 1 min.; 57° C. for 3 min.; and 72° C. for 3 min.

The 5'-end of the obtained amplified fragment was treated with NdeI and the 3'-end with BamHI, thereby producing deletion mutant pET-T604 that contains DNA coding for an amino acid sequence corresponding to the amino acid sequence of T734 but with C-terminal deletion up to Position 605.

(1-2) Expression Plasmid for High Affinity $IP_3$ Sponge "G224"

First, a gene coding for polypeptide T604 that corresponds to the first methionine (M-1) to the lysine at Position 604 (K-604) of polypeptide T734 was prepared. Specifically, site-directed mutagenesis was conducted by PCR using a complementary oligonucleotide (Yoshikawa F. et al., *J Biol Chem*, 271:18277–18284, 1996) to introduce a stop codon (TAA) and a subsequent EcoRI recognition site (GAATCC) at Position 605 of T734.

```
Sense primer:
                                        (SEQ ID NO: 5)
5'-TGTCAGACATATGCGTGTTGGAA-3'
        NdeI Antisense primer:
                                        (SEQ ID NO: 7)
5'-CCGGAATTCTTATTTCCGGTTGTTGTGGAGCAGGG-3'
     EcoRI
```

The PCR was conducted under the same conditions as described in (1-1) above.

The 5'-end of the thus-obtained amplified fragment was treated with NdeI and the 3'-end with ECORI, thereby producing deletion mutant pET-T604e that contains DNA coding for an amino acid sequence corresponding to the amino acid sequence of T734 but with C-terminal deletion up to Position 605.

Then, using deletion mutant pET-T604e as a template, site-directed mutagenesis was performed to introduce BamHI recognition site (GGATCC) immediately before the methionine at Position 224 of polypeptide T604.

```
Antisense primer:
                                        (SEQ ID NO: 7)
5'-CCGGAATTCTTATTTCCGGTTGTTGTGGAGCAGGG-3'
     EcoRI Sense primer:
                                        (SEQ ID NO: 8)
5'-CGCGGATCCATGAAATGGAGTGATAACAAAGACGACA-3'
     BamHI
```

The PCR was conducted under the same conditions as described in (1-1) above.

The thus-obtained amplified fragment (plasmid introduced with mutation) was cleaved with BamHI and EcoRI, thereby obtaining a cDNA fragment coding for Amino acids 224–604. This cDNA fragment was ligated to BamHI-EcoRI site of GST fusion plasmid (pGEX-2T) without a frameshift (in-frame), thereby obtaining plasmid pGEX-G224. Plasmid pGEX-G224 expresses fusion polypeptide G224 (FIG. 1) that includes polypeptide GST and subsequent polypeptide M-224 to K-604.

(1-3) Expression Plasmid for Low Affinity IP$_3$-binding Polypeptide

Site-directed mutagenesis was conducted by sequential PCR using pGEX-G224 as a template.

The following two mismatched oligonucleotides were synthesized to introduce mutation (K508A) at Position 508 of T604 where alanine was substituted for lysine (K-508):

5'-GAGAGCGGCAGGCACTGATGAGGG-3'(SEQ ID NO: 9)

5'-CCCTCATCAGTGCCTGCCGCTCTC-3'(SEQ ID NO: 10)

Using the above primers, site-directed mutagenesis was conducted by sequential PCR. The PCR conditions and the composition of the reaction solution were as follows:

Primary Reaction 1

```
Sense primer:
                                        (SEQ ID NO: 9)
5'-GAGAGCGGCAGGCACTGATGAGGG-3'

Antisense primer:
                                        (SEQ ID NO: 7)
5'-CCGGAATTCTTATTTCCGGTTGTTGTGGAGCAGGG-3'
     EcoRI
```

The PCR was conducted under the same conditions as described in (1-1) above.

Primary Reaction 2

```
Sense primer:
                                        (SEQ ID NO: 8)
5'-CGCGGATCCATGAAATGGAGTGATAACAAAGACGACA-3'
     BamHI Antisense primer:
                                        (SEQ ID NO: 10)
5'-CCCTCATCAGTGCCTGCCGCTCTC-3'
```

The PCR was conducted under the same conditions as described in (1-1) above.

Secondary Reaction

Ten µl of the PCR reaction product resulting through Primary reactions 1 and 2, and 1 µM each of primers (SEQ ID NOS: 7 and 8) were used to conduct PCR under the same conditions as the primary reactions.

The obtained amplified fragment was cleaved with BamHI and EcoRI. The cleaved fragment was ligated to BamHI-EcoRI site of GST fusion plasmid pGEX-2T without a frameshift (in frame), thereby obtaining plasmid pGEX-G224-m30. This mutant plasmid expresses polypeptide G224-m30 having the point mutation K508A (FIG. 1, m30).

(1-4) Expression Plasmid for High Affinity IP$_3$ Sponge "G224-m49"

Using pGEX-G224 as a template, site-directed mutagenesis was conducted by sequential PCR.

The following two mismatched oligonucleotides were synthesized to introduce a mutation (R441Q) at Position 441 of T604 where glutamine was substituted for arginine (R-441).

5'-GCTGAGGTTCAAGACCTGGACTTTG-3'(SEQ ID NO: 11)

5'-AAAGTCCAGGTCTTGAACCTCAGC-3'(SEQ ID NO: 12)

Primary Reaction 1

```
Sense primer:
                                        (SEQ ID NO: 11)
5'-GCTGAGGTTCAAGACCTGGACTTTG-3'

Antisense primer:
                                        (SEQ ID NO: 7)
5'-CCGGAATTCTTATTTCCGGTTGTTGTGGAGCAGGG-3'
     EcoRI
```

The PCR was conducted under the same conditions as described in (1-3) above.

Primary Reaction 2

```
Sense primer:
                                        (SEQ ID NO: 8)
5'-CGCGGATCCATGAAATGGAGTGATAACAAAGACGACA-3'
     BamHI Antisense priiner:
                                        (SEQ ID NO: 12)
5'-AAAGTCCAGGTCTTGAACCTCAGC-3'
```

The PCR was conducted under the same conditions as described in (1-3) above.

Ten μl of the PCR reaction product resulting through Primary reactions 1 and 2, and 1 μM each of primers (SEQ ID NOS: 6 and 8) were used to conduct PCR under the same conditions as those of the primary reactions.

The obtained amplified fragment was cleaved at a BamHI-ECORI site. The cleaved fragment was ligated to BamHI-ECORI site of GST fusion plasmid pGEX-2T without a frameshift (in frame), thereby obtaining plasmid pGEX-G224-m49. This mutant plasmid expresses polypeptide G224-m49 having the point mutation R441Q (FIG. 1, m49).

Example 2

Expression and Preparation of High Affinity IP$_3$-Binding Polypeptide with *E.coli*

Since the IP$_3$-binding core mostly results in insoluble inclusion bodies, the expression amount is low. Thus, the present inventors have modified the IP$_3$-binding region through gene engineering to produce a high affinity IP$_3$-binding polypeptide which is of lower molecule, which is capable of stable mass-expression, which can be recovered as a soluble protein, which has a higher affinity, and which has as high specificity as a conventional IP$_3$ receptor.

By low-temperature cultivation (16–22° C.), polypeptide T734 can be mass-expressed in a stable manner with a relatively high soluble fraction recovery (Kd=50±2.4 nM, Bmax=46 pmol/mg protein, 1.85 mg/l *E.coli* culture (corresponding to about 0.5 g of wet *E.coli*)). However, the inclusion bodies amount to more than ten times the amount of the soluble fraction (Yoshikawa F. et al., *J. Biol Chem.* 271: 18277–18284, 1996).

First of all, smaller polypeptides that had the above-described characteristics were prepared.

The pET-type and pGEX-type expression plasmids obtained in Example 1 were introduced into *E.coli* BL21 (DE3) and JM109, respectively, by transformation method. Expression induction with IPTG and preparation of expression proteins from *E.coli* were mainly conducted by modifying the method of Yoshikawa et al (Yoshikawa F. et al., *J. Biol Chem.* 271: 18277–18284, 1996).

Specifically, *E.coli* introduced with respective plasmids were shake cultured in L broths (containing 100 pg/ml ampicillin) at 22° C. When the absorption OD$_{600}$ became about 1.5, IPTG was added to 0.5 mM. After a few hours of shake culture at 16° C., each of the *E.coli* was recovered through centrifugation and suspended in PBS containing protease inhibitors (1 mM PMSF, 10 μM leupeptin, 1 μM pepstatin A, 2 μg/ml aprotinin). Each of the *E.coli* was disrupted by sonication. Then, each supernatant containing the expression polypeptide (soluble fraction) was collected by ultracentrifugation (Beckman Ti35 rotor, 25,000 rpm, 1 hr., 4° C.).

GST fusion polypeptides were purified from the soluble fractions by affinity purification using Glutathione-Sepharose column (Pharmacia LKB). Specifically, each of the GST fusion polypeptides was eluted from the column with 10 nM glutathione/50 mM Tris-HCl (pH 8.0) by mainly following the manual provided by the manufacturer. The polypeptide solutions were equilibrated with 10 mM HEPES-KOH (pH 7.2), 88 mM NaCl and 1 mM KCl using PD10 desalted column (Pharmacia LKB), and then dispensed, thereby obtaining the IP$_3$ sponges (FIG. 1: G224, m30, m49 and GST). The IP$_3$ sponges were stored at −80° C. until they were used.

A series of deletion mutants based on polypeptide T734 were prepared by serially shortening the length of the polypeptide T734 from the C-terminus. The analysis of the deletion mutants indicated that T705 and T699 had no marked characteristic difference with T734. In the cases of polypeptides T569, T572 and T576, the expression amounts of the soluble proteins were lower than T734. Stable mass-expression of soluble protein was successful with polypeptide T604 which was obtained by deleting the C-terminus of T734 up to Amino acid 605 (FIG. 1).

With reference to FIG. 1, the uppermost (IP$_3$R1) is the N-terminal amino acids of the IP$_3$ receptor including the IP$_3$-binding core region (core: Amino acids 226–578). T604 (Amino acids 1–604), G224 (GST+Amino acids 224–604), G224m30 (G224 introduced with K508A mutation), G224m49 (G224 introduced with R441Q mutation), and GST (derived from pGEX-2T)) are also shown in FIG. 1.

T604 had a [$^3$H]IP$_3$-binding activity substantially equivalent to that of T734 (Kd=45 nM), and a higher yield of soluble protein (Bmax=690 pmol/mg protein). Specifically, the yield was 19 mg/l *E.coli* culture (FIGS. 2B and 2C, Table 1).

TABLE 1

Expression of IP$_3$-binding site in *E.coli*

| Protein | Expression efficiency (mg/l *E.coli* culture) | Kd [nM] | B$_{max}$ [pmol/μg purified protein] |
|---|---|---|---|
| Purified IP$_3$R[a] | — | 83 | 2.1 |
| T734[b] | 1.85 | (50)[c] | ND |
| T604 | 19 | 7.6/(45)[c] | ND |
| G224 | 30 | 0.083 | 1.6 |
| G224m49 | ND | 0.043 | 1.7 |
| G224m30 | ND | 330 | 3.0 | a. Maeda et al., EMBO J. 9, 51–67, 1990
b. Yoshikawa et al., J. Biol. Chem., 271, 18277–18284, 1996
c. the values in parentheses represent Kd obtained from crude cell lysates
ND. Not Determined The total expression amount of polypeptide T604 substantially equaled to that of polypeptide T734 but T604 had a remarkably improved soluble protein yield. The yield of soluble protein of polypeptide T604 was substantially the same at 30° C. and 37° C., and reached the peak within 2 hours after initiating expression induction.

FIG. 2A shows the result of Western blotting analysis of the protein (0.1 μg) obtained from an *E.coli* extract solution (soluble fraction) that expresses polypeptide T604 (66 kDa). As a control, a cell extract solution obtained by transforming a vector that does not include T604 (pET-3a) was used. FIG. 2B shows a comparison of the total amounts of specific IP$_3$-binding contained in 0.7 μl soluble fractions, for T734, T604, and the control vector. FIG. 2C shows the result of Schatchard plot analysis where the binding between 3 μg of T604 soluble fraction and 9.6 nM [$^3$H]IP$_3$ was competitively inhibited with non-labeled IP$_3$ (cold IP$_3$) at various concentrations. The results were Kd=45±7.6, B$_{max}$=690±64 pmol/mg protein.

When T734 was serially deleted from the N-terminus, a very short N-terminal deletion of T734 (e.g., a deletion of 31 amino acids) caused lack of IP$_3$-binding activity even the deletion was outside the core region. However, the polypeptide retrieved the IP$_3$-binding activity when the N-terminus was deleted to Amino acid 220–225, near the N-terminus of the core region (Yoshikawa et al, 1996). The theory for this is unknown, but presumably, the formation of the three-dimensional structure for active core region is somehow interrupted depending on the degree of deletion. Although the active polypeptide with the N-terminal deletion up to Amino acid 220–225 had a relatively high affinity, the amount of soluble protein expressed was lower.

As described above, a protein obtained by deleting Amino acids 1–223 of polypeptide T604 (N4-T604; Amino acids 224–604) had a higher activity (about 3 times high) but lower production than those of the original T604. Accordingly, polypeptide T604 seemed to be the most suitable polypeptide for stably mass-expressing only the high affinity $IP_3$-binding region as a soluble protein.

Example 3

Expression of $IP_3$ Sponge (i) [$^3$H]-$IP_3$-binding Inhibition Experiment

Based on the results obtained in Example 2, an $IP_3$-binding polypeptide with a higher affinity was produced. As described above, when the amino-terminal Amino acids 1–223 of polypeptides T604 and T734 were deleted, high [$^3$H]$IP_3$-binding activities were obtained. Even Amino acid region 224–579 (a polypeptide that almost corresponds to the core region) consisting of only 356 amino acid residues has an affinity as high as Kd=2.3 nM (Yoshikawa et al., 1996, supra). However, as described above, these polypeptides have lower soluble protein expression levels. In other words, longer amino terminal deletion may result in a higher affinity on one hand, but it also lowers the expression amount and expression stability of soluble proteins by rendering most of proteins as insoluble inclusion bodies.

In general, stability, solubility and an expression level of a foreign polypeptide are known to be improved when it is made into a GST fusion body. In this example, fusion proteins G224, G224-m30 and G224-m49 consisting of GST and an $IP_3$-binding site (Amino acid region 224–604) were prepared by ligating GST to replace the N-terminal region (Amino acids 1–223) of the $IP_3$ receptor (FIG. 1)

The $IP_3$-binding activities of these fusion proteins were measured mainly by the method of Yoshikawa et al (1996).

Each fusion protein ($IP_3$ sponge) (0.2 µg) was mixed with 100 µl of binding buffer-α (50 mM Tris-HCl (pH 8.0 at 4° C.), 1 mM EDTA, 1 mM β-mercaptoethanol) that contained 9.6 nM D-myo-[$^3$H](1,4,5)$IP_3$ (777 GBq/mmol; DuPont NEN) (hereinafter, abbreviated as "[$^3$H]$IP_3$") and various concentrations of non-labeled D-myo-(1,4,5)$IP_3$ (Dojindo) (hereinafter, abbreviated as "cold $IP_3$"). The mixture was left to stand on ice for 10 minutes. To the mixture, 4 µl of 50 mg/ml γ-globulin (Sigma) (final concentration: 1 mg/ml) and 100 µl of 30% PEG 6000 (Sigma)/binding buffer-a solution (final concentration: 15%) were added. The resultant mixture was left to stand on ice for 5 minutes, and then centrifuged at 10,000×g at 2° C. for 5 minutes to collect polypeptide/PEG complex. PEG-precipitated [$^3$H]$IP_3$-binding polypeptide was well solubilized with 180 µl solubilizer Solvable, (DuPont NEN). The resultant was neutralized with 18 µl glacial acetic acid and then added to 5 ml liquid scintillation counter (Atomlight [DuPont NEN]) to measure the radioactivity (first radioactivity). Non-specific binding of each protein was determined by measuring the second radioactivity in the presence of 2 µM or 10 µM cold $IP_3$. Then, a specific binding value of each protein was obtained by subtracting the second radioactivity (non-specific binding value) from the first radioactivity values.

Scatchard plot analysis was conducted under the following conditions. For low-affinity polypetides (G224-m30 and control GST), the binding experiment was conducted in 100 µl binding buffer a by adding 9.6 nM [$^3$H]$IP_3$ (DuPont NEN) and 10–20 nM of cold $IP_3$ to 2 µg of $IP_3$-binding polypeptide, and by adding 9.6 nM [$^3$H]$IP_3$ (DuPont NEN) and 50 nM-2 µM of cold $IP_3$ to 0.01 µg $IP_3$-binding polypeptide. For high-affinity $IP_3$ sponges (G224 and G224-m49), binding experiment was conducted with 0.02 µg $IP_3$ sponges at [$^3$H]-$IP_3$ concentrations of 0.15, 0.3, 0.6, 1.2, 2.4, 4.8 and 9.6 nM without adding cold $IP_3$.

The inhibition effects of the $IP_3$-binding polypeptides ($IP_3$ sponges) on [$^3$H]$IP_3$-binding activity of cerebellar microsome was analyzed as follows.

A microsomal fraction was prepared from the cerebella of mice ddY (Nippon SLC) mainly by following the method of Nakada et al. (Nakada S. et al., Biochem. J. 277:125–131, 1991). In 100 µl of binding buffer a, various concentrations of the $IP_3$ sponges were added respectively to see the changes in the binding between the cerebellar microsome (40 µg) and 9.6 nM [$^3$H]-$IP_3$ according to the above method (see Scatchard plot analysis).

Figure 3A:
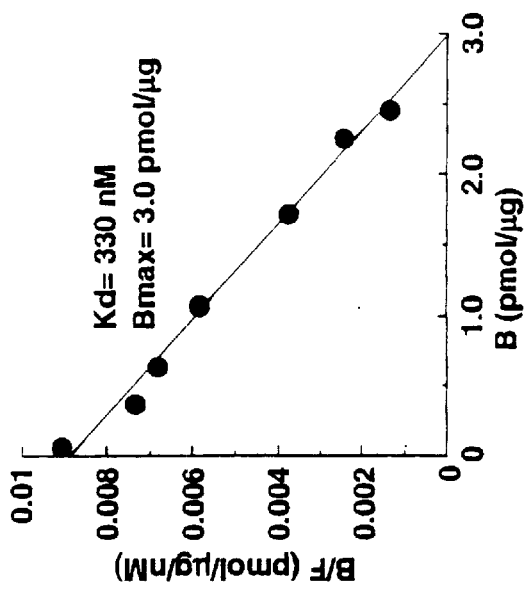
FIGS. 3A–3C are graphs showing the $IP_3$-binding activities of the $IP_3$ sponges.
Figure 3B:
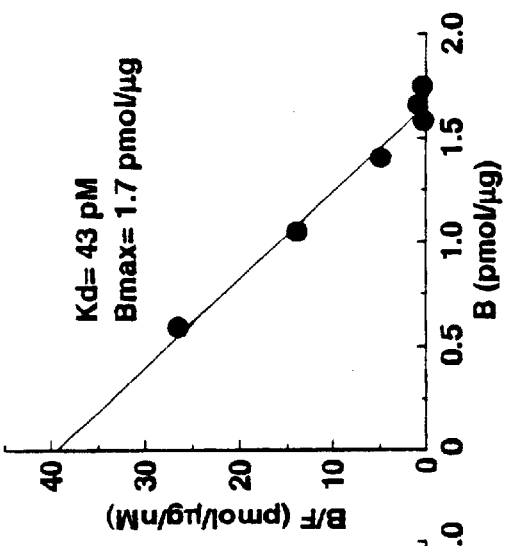
Figure 3C:
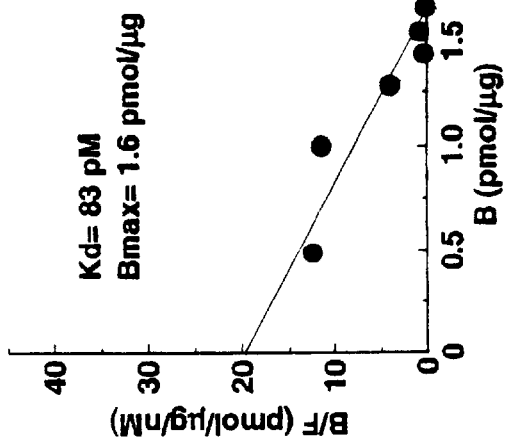

As a result, the affinity of polypeptide G224 was found out to be 500 times higher than that of polypeptide T734 (Kd=83 pM, $B_{max}$=1.6 pmol/µg protein) (FIG. 3A). Polypeptide G224 binds well to (1,4,5)$IP_3$ and (2,4,5)$IP_3$ and the yield of $IP_3$-binding protein was about 30 mg/l E.coli culture (Table 1) After purifying the protein with a glutathione column and a subsequent PD10 column, the yield was about 24 mg/l. The binding activity was augmented when R441Q mutation was introduced into polypeptide T734 (Yoshikawa et al., 1996, supra). The affinity of polypeptide G224-m49 (G224 introduced with R441Q mutation) doubled and became about 1,000 times higher than that of polypeptide T734 (Kd=about 43 pM, $B_{max}$=1.7 pmol/µg protein) (FIG. 3B, Table 1). The binding activity decreased when polypeptide T734 was introduced with K508A mutation (Yoshikawa et al., 1996 (supra)). Similarly, the binding activity of polypeptide G224-m30 decreased when G224 was introduced with K508A mutation and became as low as about 1/4,000 of polypeptide G224 and about 1/7,700 of polypeptide G224-m49 (Kd=about 330 nM, $B_{max}$=3.0 pmol/µg protein) (FIG. 3C, Table 1)

(ii) $IP_3$-binding Inhibition via Absorption by Novel $IP_3$ Sponge $IP_3$-binding polypeptides G224 and G224-m49 have powerful $IP_3$-binding activities that are 500 to 1,000 times higher than that of the original $IP_3$ receptor. Polypeptides G224 and G224-m49 were tested for their use as an $IP_3$-specific absorption body (sponge) ($IP_3$ sponge), i.e., whether they can decrease the amount of $IP_3$-binding by the $IP_3$ receptors in a solution by competitively absorbing $IP_3$ in the solution (FIG. 4).

Mouse cerebellum is a tissue that is rich in $IP_3$ receptor and whose microsomal fraction has a [$^3$H]$IP_3$-binding activity which is at least 50 times higher than those in other tissues (Maeda et al., 1990 (supra)). Binding between 40 µg cerebellar microsome (Kd=21 nM, $B_{max}$=23 pmol/mg protein) and 9.6 nM [$^3$H]$IP_3$ in 100 µl solution was analyzed for percentage (%) of competitive inhibition at various concentrations of $IP_3$ sponges where the activity under the absence of $IP_3$ sponge was considered 100%. It was calculated that, there were about 0.92 pmol of $IP_3$-binding site of cerebellum $IP_3$ receptor and 0.96 pmol of [$^3$H]$IP_3$ present in the 100 µl solution.

Figure 4:
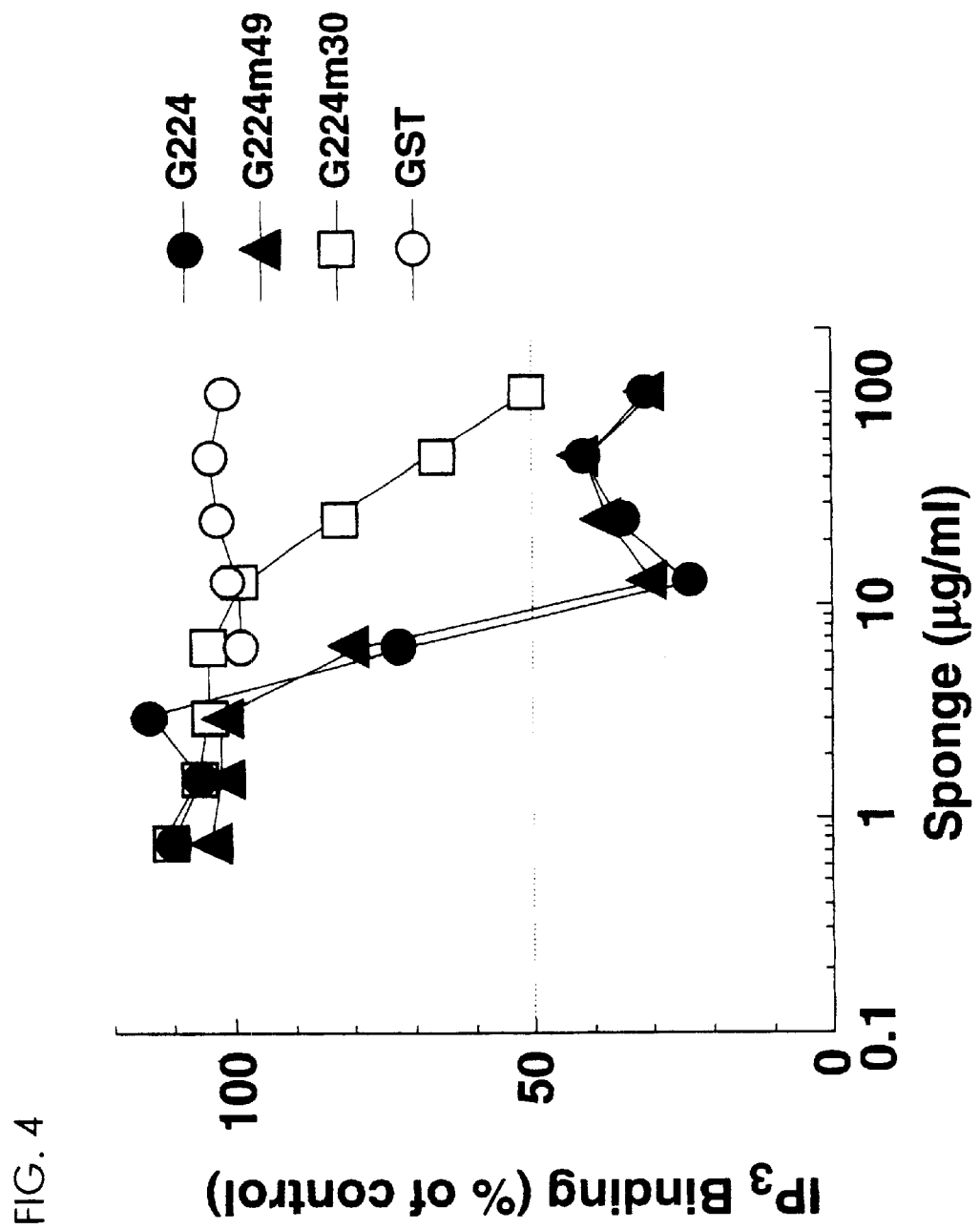
FIG. 4 is a graph showing a curve of $IP_3$-binding inhibition depending on the $IP_3$ sponge concentration.

As a result, no inhibition effect was observed for control GST even when the $IP_3$ sponge concentration was 100 µg/ml (FIG. 4). On the other hand, for high-affinity polypeptides G224 and G224-m49, strong $IP_3$-binding inhibition activities were observed and $IC_{50}$ was about 10 µg/ml (FIG. 4). Polypeptide G224-m30 with low affinity had low inhibition activity with $IC_{50}$ of 100 µg/ml. According to this in vitro experiment system, the $IP_3$ sponge tended to precipitate with the microsome membrane when the $IP_3$ sponge concentration exceeded about 25 µg/ml, and so the concentration-dependent curves were likely to fluctuate (FIG. 4). Thus, the apparent inhibition of G224-m30 observed at $IP_3$ sponge concentration exceeding 25 µg/ml could be due to precipitation under high concentration.

These results show that [$^3$H]$IP_3$-binding of the $IP_3$ receptor can efficiently be inhibited according to the binding affinity and the concentration of the $IP_3$ sponge used.

High affinity $IP_3$-binding polypeptide of the invention is a novel $IP_3$ sponge that can be used as an $IP_3$ neutralizing agent, or an antagonist for $IP_3$-induced calcium.

Example 4

Test of Inhibiting $IP_3$-Induced $Ca^{2+}$ Release (IICR)

To conduct a test of inhibiting $IP_3$-induced $Ca^{2+}$ release, a microsomal fraction was prepared from mouse cerebellum as described in Example 3. The fraction was suspended in Buffer B, dispensed, and stored at −80° C. until it was used.

Composition of Buffer B was 110 mM KCl, 10 mM NaCl, 5 mM $KH_2PO_4$, 1 mM DTT, and 50 mM HEPES-KOH (pH 7.2) (containing a cocktail of protease inhibitors [0.1 mM PMSF, 10 µM leupeptin, 10 µM pepstatin A, 10 µM E-64] and 2 mM $MgCl_2$).

An $IP_3$-induced $Ca^{2+}$ release activity of cerebellar microsome was determined by using fura-2 (Molecular Probe) as a fluorescent $Ca^{2+}$ indicator. Specifically, excitations upon addition of $IP_3$ at two wavelengths (340 nm and 380 nm) were measured with fluorescence spectrophotometer CAF110 (Nihon Bunko) to see the change in the fluorescent intensity ratio (F340/F380) at 500 nm.

$IP_3$-induced $Ca^{2+}$ release from the cerebellar microsome is generally $EC_{50}$=100–200 nM $IP_3$. Cerebellar microsome (100 pg) was mixed with 500 µl of a release buffer (Buffer B containing 1 mM $MgCl_2$, 2 µM fura-2, 1 mM DTT, 10 mM creatine phosphate, 40U/ml creatine kinase, 1 µg/ml oligomycin, and the cocktail of protease inhibitors) in a measurement cuvette with a stirrer bar. The following reaction was conducted at 30° C. while constantly stirring with the stirrer bar.

One mM of ATP was added to the mixture in the cuvette to activate $Ca^{2+}$ pumping ($Ca^{2+}$-ATPase), whereby $Ca^{2+}$ was incorporated into the inner space of microsome ($Ca^{2+}$ loading). $Ca^{2+}$ loading was confirmed by monitoring until the decrease of fura-2 fluorescent level became constant. The change in the fura-2 fluorescent intensity ratio was measured (F340/F380) at a subthreshold level.

The effect of $IP_3$ sponge on inhibiting $IP_3$-induced $Ca^{2+}$ release activity of cerebellar microsome was analyzed as follows. After the addition of ATP, the curve of fura-2 fluorescent intensity was monitored until the decrease became constant. Then, various concentrations of $IP_3$ sponges were added. After 1 min., 50 nM to 1 µM of $IP_3$ was added to the reaction mixture to observe the change of fura-2 fluorescent intensity induced by the $IP_3$.

The $IP_3$ sponge concentration dependency was determined as follows. High affinity polypeptide G224 of 3.125, 6.25, 12.5, 25, 50, 100, 200 µg/ml were added to the reaction mixture, respectively. After about 1 min., 100 nM of $IP_3$ was added to measure the $Ca^{2+}$ release activity induced by the $IP_3$. The concentration dependency of low affinity polypeptide G224-m30 was determined by adding G224-m30 of 200, 400 and 500 µg/ml. After about 1 min., 100 nM of $IP_3$ was added to measure the $Ca^{2+}$ release activity induced by the $IP_3$. In addition, G224-m30 of 500 µg/ml was also added, and after about 1 min., 50 nM of $IP_3$ was added to measure the $Ca^{2+}$ release activity induced by the $IP_3$.

As a result, it was found that the $IP_3$ sponges specifically inhibited in a competitive manner the $IP_3$-binding by the $IP_3$ receptor of cerebellar microsome by absorbing the $IP_3$ (FIGS. 5A–5F, 6A–6G and 7). In FIGS. 5A–5F and 6A–6G, the vertical axis represent the change in fura-2 fluorescent intensity ratio (F340/F380) (i.e., change in the amount of $Ca^{2+}$), and the horizontal axis represents the time (sec).

Figure 5E:
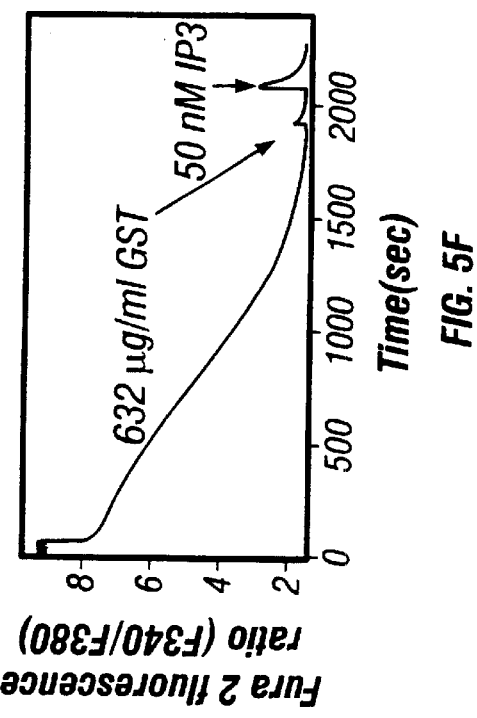
Figure 5F:
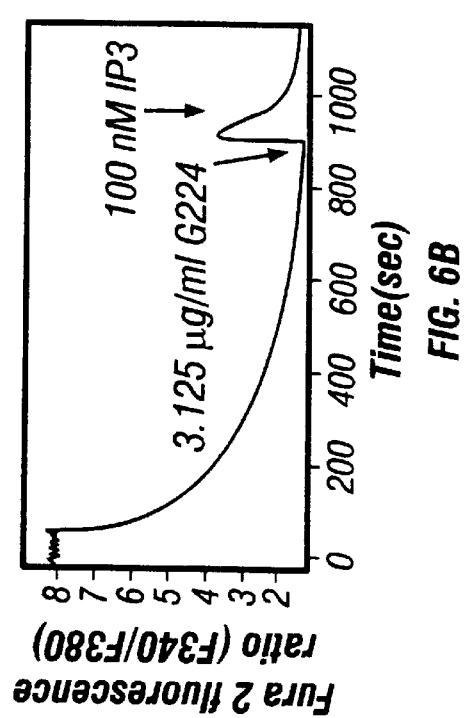

As shown in FIGS. 5A, 5B and 5C, in the absence of $IP_3$ sponge (controls), $IP_3$-induced $Ca^{2+}$ release activities were dependent on $IP_3$ concentration. Low-affinity polypeptide G224-m30 at a concentration of 500 µg/ml had no inhibiting effect on $Ca^{2+}$ release with 100 nM $IP_3$ (FIG. 5E). Little difference was found between G224-m30 and the control for effects on inhibiting 50 nM $IP_3$ (FIG. 5E). With GST only, even at a high concentration of 632 µg/ml, no change was seen in $Ca^{2+}$ release activity induced with 50 nM $IP_3$ (FIG. 5F) Thus, in each case, no marked difference was noted with the control.

Figure 6A:
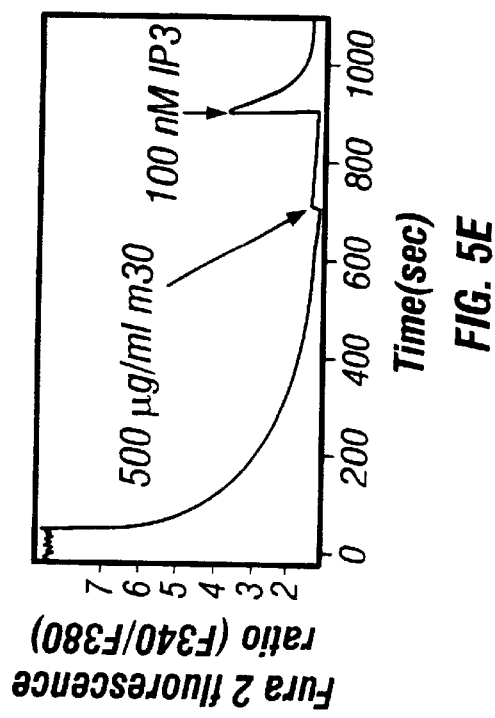
FIGS. 6A–6G are graphs showing the effect of high affinity IP$_3$ sponge G224 on inhibition of IP$_3$-induced Ca$^{2+}$ release.
Figure 6B:
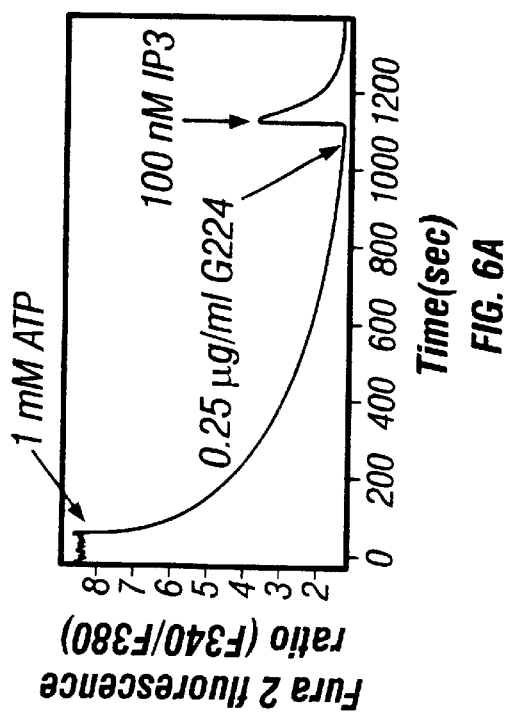
Figure 6D:
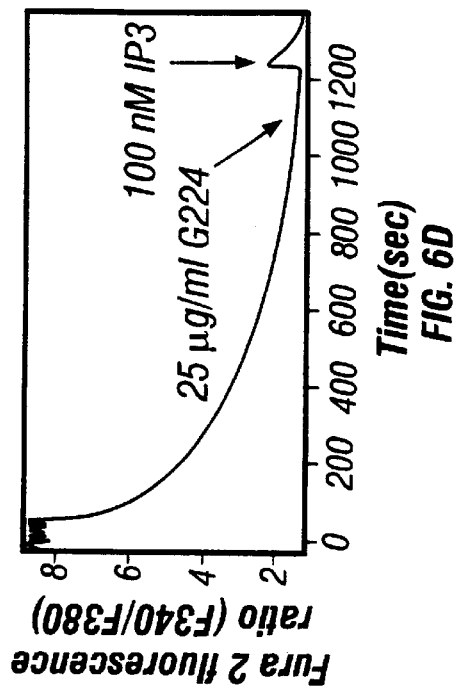
Figure 6C:
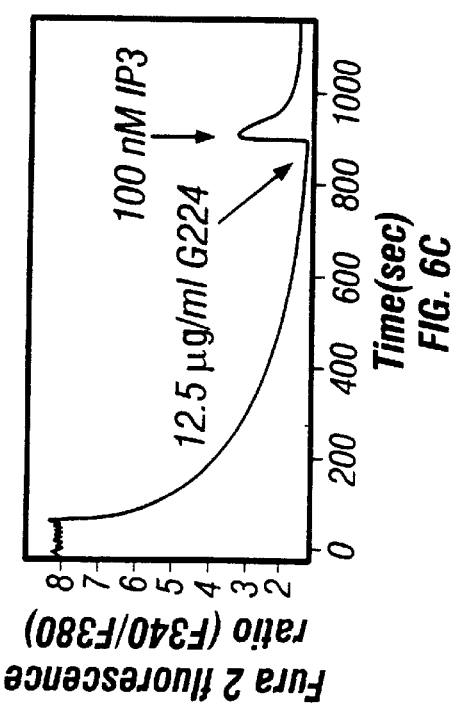
Figure 6E:
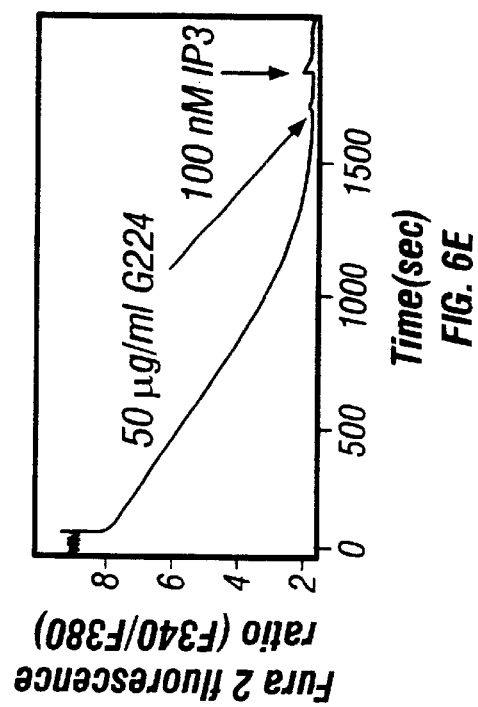
Figure 6G:
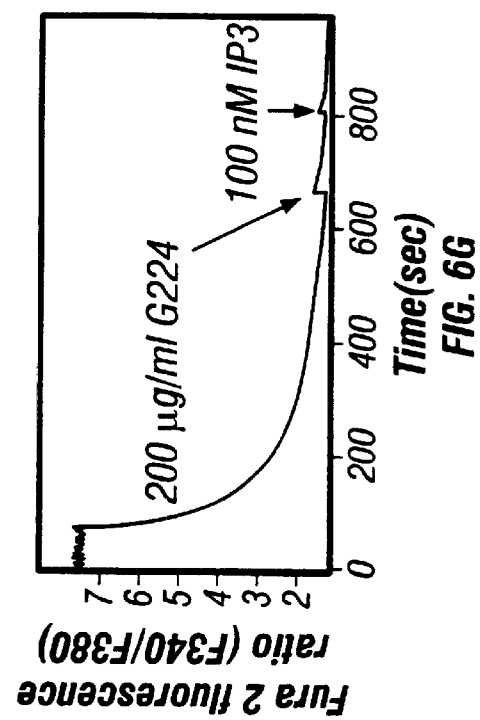
Figure 6F:
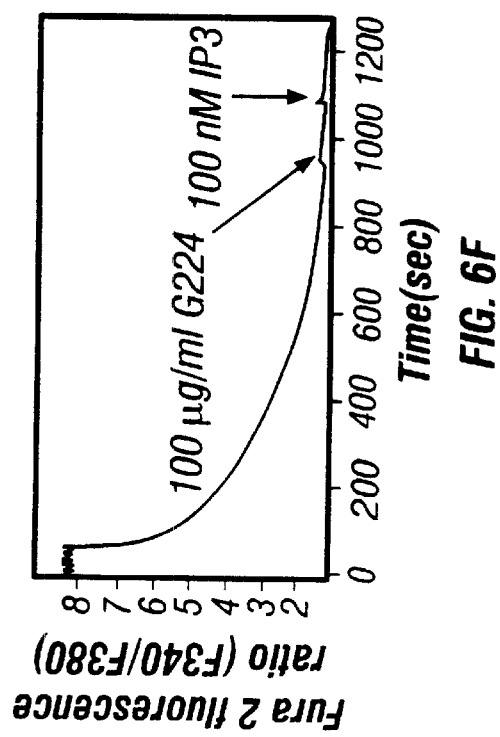

On the contrary to the above results, high affinity polypeptide G224 had a significant inhibition effect on $IP_3$-induced $Ca^{2+}$ release depending on its concentration (FIGS. 6A–6G). The high affinity polypeptide G224 had the greatest inhibition effect at 100 µg/ml and almost completely inhibited the $IP_3$-induced $Ca^{2+}$ release (FIG. 6F).

Figure 7:
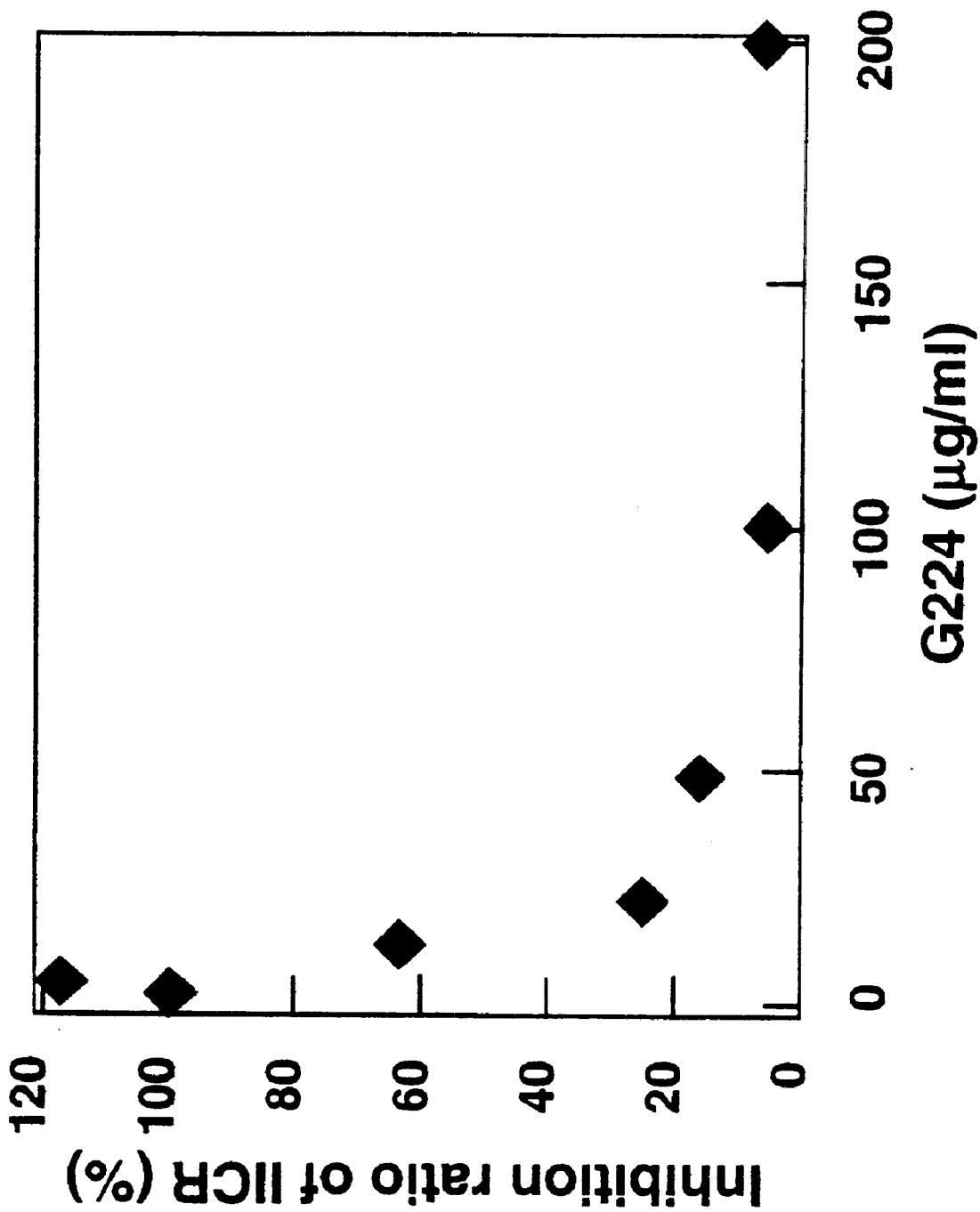
FIG. 7 is a plot diagram showing an IP$_3$-induced Ca$^{2+}$ release depending on the concentration of the high affinity IP$_3$ sponge G224.

The peak values of $Ca^{2+}$ release obtained by adding G224 at each concentration shown in FIGS. 6A–6G, were plotted where the peak obtained in the absence of G224 was considered 100 % (FIG. 7). The horizontal axis represents each concentration of polypeptide G224 and the verticle axis represents the peak value of $Ca^{2+}$ release. As can be appreciated from FIG. 7, the concentration of polypeptide G224 required for 50 % inhibition of $IP_3$-induced $Ca^{2+}$ release was about 20 µg/ml.

Accordingly, it was found that the high affinity $IP_3$-binding polypeptide acted as an $IP_3$ sponge and specifically inhibited, in a concentration-dependant manner, the $IP_3$-induced $Ca^{2+}$ release by the $IP_3$ receptor on cerebellar microsome.

The present invention provides a polypeptide having a high affinity binding activity to inositol 1,4,5-trisphosphate, a gene encoding the polypeptide, a recombinant vector including the gene, a transformant including the vector and a method for producing the polypeptide.

The polypeptide of the invention can be used to control the inhibition of a specific cell function that depends on an $IP_3$-induced calcium signal transmission ($IP_3$ neutralizing agent, antagonist for $IP_3$-induced calcium, etc.). Furthermore, the polypeptide and the gene of the present invention is useful as an $IP_3$ signal detecting agent for inhibiting activation of $IP_3$-induced calcium signal transmission. The gene of the invention is also useful as a therapeutic agent for treating a disease associated with calcium production.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

All publications, patents, and patent applications cited herein are incorporated herein by reference in their entirety.

What is claimed is:

1. An isolated nucleic acid coding for a polypeptide consisting of an amino acid sequence of position 224 to 604 in SEQ ID NO:4.

2. A recombinant vector comprising the nucleic acid as set forth in claim 1.

3. A transformant comprising the recombinant vector as set forth in claim 2.

4. A method for producing a polypeptide which binds to an inositol 1,4,5-trisphosphate, comprising:
   culturing the transformant of claim 3 under conditions wherein the transformant expresses the polypeptide; and
   collecting the polypeptide from the cultured transformant, thereby producing a polypeptide which binds to an inositol 1,4,5-trisphosphate.

5. An isolated nucleic acid coding for a polypeptide consisting of an amino acid sequence of position 224 to 604 in SEQ ID NO:4, wherein the arginine at position 441 of SEQ ID NO:4 is replaced with glutamine.

6. An isolated nucleic acid consisting of a nucleotide sequence of residue 998 to 2140 in SEQ ID NO:3.

7. An isolated nucleic acid coding for a polypeptide consisting of an amino acid sequence of position 1 to 604 in SEQ ID NO:4.

8. The isolated nucleic acid of claim 7 consisting of a nucleotide sequence of residue 329 to 2140 in SEQ ID NO:3.

9. A recombinant vector comprising the isolated nucleic acid of claim 5.

10. A transformant comprising the recombinant vector of claim 9.

11. A method for producing a polypeptide which binds to an inositol 1,4,5-trisphosphate, comprising:
    culturing the transformant of claim 10 under conditions wherein the transformant expresses the polypeptide; and
    collecting the polypeptide from the cultured transformant, thereby producing a polypeptide which binds to an inositol 1,4,5-trisphosphate.

12. A transformed bacterium comprising the recombinant vector of claim 9.

13. The transformed bacterium of claim 12, wherein the transformed bacterium is an *E. coli*.

14. A recombinant vector comprising the isolated nucleic acid of claim 7.

15. A transformant comprising the recombinant vector of claim 14.

16. A method for producing a polypeptide which binds to an inositol 1,4,5-trisphosphate, comprising:
    culturing the transformant of claim 15 under conditions wherein the transformant expresses the polypeptide; and
    collecting the polypeptide from the cultured transformant, thereby producing a polypeptide which binds to an inositol 1,4,5-trisphosphate.

17. An isolated nucleic acid coding for a polypeptide consisting of an amino acid sequence starting at position 224 of SEQ ID NO:4 and extending to at least position 579 of SEQ ID NO:4 and at most position 604 of SEQ ID NO:4.

18. An isolated nucleic acid coding for a polypeptide consisting of a glutathione S-transferase and an amino acid sequence of position 224 to 604 in SEQ ID NO:4.

19. An isolated nucleic acid coding for a polypeptide consisting of a glutathione S-transferase and an amino acid sequence of position 224 to 604 in SEQ ID NO:4, wherein the arginine at position 441 of SEQ ID NO:4 is replaced with glutamine.

20. An isolated nucleic acid coding for a polypeptide consisting of an amino acid sequence of position 224 to 604 in SEQ ID NO:4, wherein the arginine at position 441 of SEQ ID NO:4 is replaced with a glutamine, and the polypeptide is encoded by a sequence as set forth in SEQ ID NO:3, and the arginine at position 441 is replaced with the glutamine by replacing nucleotides "gg" at positions 1650 to 1651 of SEQ ID NO:3 with an "aa" or an "ag."

21. An isolated nucleic acid coding for a polypeptide consisting of a glutathione S-transferase and an amino acid sequence of position 224 to 604 in SEQ ID NO:4, wherein the arginine at position 441 of SEQ ID NO:4 is replaced with a glutamine, and the polypeptide is encoded by a sequence as set forth in SEQ ID NO:3, and the arginine at position 441 is replaced with the glutamine by replacing nucleotides "gg" at positions 1650 to 1651 of SEQ ID NO:3 with an "aa" or an "ag."

22. An isolated nucleic acid coding for a polypeptide consisting of a glutathione S-transferase and an amino acid sequence starting at position 224 of SEQ ID NO:4 and extending to at least position 579 of SEQ ID NO:4 and at most position 604 of SEQ ID NO:4.

* * * * *

SEQUENCE LISTING

<160> NUMBER OF SEQ ID NOS: 14

<210> SEQ ID NO 1
<211> LENGTH: 1812
<212> TYPE: DNA
<213> ORGANISM: Mus musculus
<220> FEATURE:
<221> NAME/KEY: CDS
<222> LOCATION: (1)..(1812)

<400> SEQUENCE: 1

| | | | | | | | | | | | | | | | | |
|---|---|---|---|---|---|---|---|---|---|---|---|---|---|---|---|---|
| atg | tct | gac | aaa | atg | tcg | agt | ttc | cta | cat | att | gga | gac | att | tgt | tct | 48 |
| Met | Ser | Asp | Lys | Met | Ser | Ser | Phe | Leu | His | Ile | Gly | Asp | Ile | Cys | Ser | |
| 1 | | | | 5 | | | | | 10 | | | | | 15 | | |
| ctg | tat | gcg | gag | gga | tct | acg | aat | gga | ttt | atc | agc | acc | tta | ggc | ttg | 96 |
| Leu | Tyr | Ala | Glu | Gly | Ser | Thr | Asn | Gly | Phe | Ile | Ser | Thr | Leu | Gly | Leu | |
| | | | 20 | | | | | 25 | | | | | 30 | | | |
| gtt | gat | gac | cgt | tgt | gtt | gta | cag | cca | gaa | gcc | ggg | gac | ctt | aac | aat | 144 |
| Val | Asp | Asp | Arg | Cys | Val | Val | Gln | Pro | Glu | Ala | Gly | Asp | Leu | Asn | Asn | |
| | | | 35 | | | | | 40 | | | | | 45 | | | |
| cca | ccc | aag | aaa | ttc | aga | gac | tgc | ctc | ttt | aag | cta | tgt | cct | atg | aat | 192 |
| Pro | Pro | Lys | Lys | Phe | Arg | Asp | Cys | Leu | Phe | Lys | Leu | Cys | Pro | Met | Asn | |
| | | 50 | | | | | 55 | | | | | 60 | | | | |
| cga | tac | tcc | gca | cag | aaa | cag | ttc | tgg | aaa | gct | gct | aag | ccc | ggg | gcc | 240 |
| Arg | Tyr | Ser | Ala | Gln | Lys | Gln | Phe | Trp | Lys | Ala | Ala | Lys | Pro | Gly | Ala | |
| 65 | | | | | 70 | | | | | 75 | | | | | 80 | |
| aac | agc | act | aca | gat | gca | gtg | ctg | ctc | aac | aaa | ttg | cat | cat | gct | gca | 288 |
| Asn | Ser | Thr | Thr | Asp | Ala | Val | Leu | Leu | Asn | Lys | Leu | His | His | Ala | Ala | |
| | | | | 85 | | | | | 90 | | | | | 95 | | |
| gac | ttg | gaa | aag | aag | cag | aat | gag | aca | gaa | aac | agg | aaa | ttg | ttg | ggg | 336 |
| Asp | Leu | Glu | Lys | Lys | Gln | Asn | Glu | Thr | Glu | Asn | Arg | Lys | Leu | Leu | Gly | |
| | | | | 100 | | | | | 105 | | | | | 110 | | |
| acc | gtc | atc | caa | tat | ggc | aac | gtg | atc | cag | ctc | ctg | cat | ttg | aaa | agc | 384 |
| Thr | Val | Ile | Gln | Tyr | Gly | Asn | Val | Ile | Gln | Leu | Leu | His | Leu | Lys | Ser | |
| | | | 115 | | | | | 120 | | | | | 125 | | | |
| aat | aaa | tac | ctg | act | gtg | aat | aag | agg | ctc | cca | gcc | ttg | cta | gag | aag | 432 |
| Asn | Lys | Tyr | Leu | Thr | Val | Asn | Lys | Arg | Leu | Pro | Ala | Leu | Leu | Glu | Lys | |
| | | | 130 | | | | | 135 | | | | | 140 | | | |
| aat | gcc | atg | agg | gtg | acg | ttg | gac | gag | gct | gga | aat | gaa | ggg | tcc | tgg | 480 |
| Asn | Ala | Met | Arg | Val | Thr | Leu | Asp | Glu | Ala | Gly | Asn | Glu | Gly | Ser | Trp | |
| 145 | | | | | 150 | | | | | 155 | | | | | 160 | |
| ttt | tac | att | caa | cca | ttt | tac | aag | ctt | cgc | tcc | atc | gga | gac | agt | gtg | 528 |
| Phe | Tyr | Ile | Gln | Pro | Phe | Tyr | Lys | Leu | Arg | Ser | Ile | Gly | Asp | Ser | Val | |
| | | | | 165 | | | | | 170 | | | | | 175 | | |
| gtc | ata | ggc | gac | aag | gta | gtt | ttg | aat | cct | gtc | aat | gct | ggc | cag | cct | 576 |
| Val | Ile | Gly | Asp | Lys | Val | Val | Leu | Asn | Pro | Val | Asn | Ala | Gly | Gln | Pro | |
| | | | 180 | | | | | 185 | | | | | 190 | | | |
| cta | cat | gcc | agc | agt | cat | cag | ctg | gtg | gat | aac | cca | ggc | tgc | aat | gag | 624 |
| Leu | His | Ala | Ser | Ser | His | Gln | Leu | Val | Asp | Asn | Pro | Gly | Cys | Asn | Glu | |
| | | | 195 | | | | | 200 | | | | | 205 | | | |
| gtc | aac | tcc | gtc | aac | tgt | aat | aca | agc | tgg | aag | ata | gtg | ctt | ttc | atg | 672 |
| Val | Asn | Ser | Val | Asn | Cys | Asn | Thr | Ser | Trp | Lys | Ile | Val | Leu | Phe | Met | |
| | | | 210 | | | | | 215 | | | | | 220 | | | |
| aaa | tgg | agt | gat | aac | aaa | gac | gac | att | ctc | aaa | gga | ggt | gat | gtg | gtg | 720 |
| Lys | Trp | Ser | Asp | Asn | Lys | Asp | Asp | Ile | Leu | Lys | Gly | Gly | Asp | Val | Val | |
| 225 | | | | | 230 | | | | | 235 | | | | | 240 | |
| agg | ctc | ttc | cat | gcc | gag | caa | gag | aag | ttt | ctc | acc | tgt | gat | gag | cac | 768 |
| Arg | Leu | Phe | His | Ala | Glu | Gln | Glu | Lys | Phe | Leu | Thr | Cys | Asp | Glu | His | |
| | | | | 245 | | | | | 250 | | | | | 255 | | |

-continued

| | | |
|---|---|---|
| cgg aag aag cag cat gtg ttc ctg agg acc acc ggc agg cag tca gcc<br>Arg Lys Lys Gln His Val Phe Leu Arg Thr Thr Gly Arg Gln Ser Ala<br>260                       265                   270 | 816 | |
| acg tcg gcc acc agt tct aaa gcc ctg tgg gaa gtg gag gta gtc cag<br>Thr Ser Ala Thr Ser Ser Lys Ala Leu Trp Glu Val Glu Val Val Gln<br>        275                   280                   285 | 864 | |
| cac gac cca tgt cgg ggt gga gct ggg tac tgg aat agc ctc ttc cgg<br>His Asp Pro Cys Arg Gly Gly Ala Gly Tyr Trp Asn Ser Leu Phe Arg<br>290                       295                   300 | 912 | |
| ttc aag cac ctg gct aca ggg cat tac ttg gct gca gag gta gac cct<br>Phe Lys His Leu Ala Thr Gly His Tyr Leu Ala Ala Glu Val Asp Pro<br>305                       310                   315                   320 | 960 | |
| gac ttt gag gaa gaa tgc ctg gag ttt cag ccc tca gtg gac cct gat<br>Asp Phe Glu Glu Glu Cys Leu Glu Phe Gln Pro Ser Val Asp Pro Asp<br>                  325                   330                   335 | 1008 | |
| cag gat gca tct cgg agt agg ttg aga aac gcg caa gaa aaa atg gta<br>Gln Asp Ala Ser Arg Ser Arg Leu Arg Asn Ala Gln Glu Lys Met Val<br>                340                   345                   350 | 1056 | |
| tac tct ctg gtc tcc gtg cct gaa ggc aac gac atc tcc tcc atc ttt<br>Tyr Ser Leu Val Ser Val Pro Glu Gly Asn Asp Ile Ser Ser Ile Phe<br>355                       360                   365 | 1104 | |
| gag cta gac ccc acg act ctg cgt gga ggt gac agc ctt gtc cca agg<br>Glu Leu Asp Pro Thr Thr Leu Arg Gly Gly Asp Ser Leu Val Pro Arg<br>370                       375                   380 | 1152 | |
| aac tcc tat gtc cgt ctc aga cac ctg tgc acc aac acc tgg gta cac<br>Asn Ser Tyr Val Arg Leu Arg His Leu Cys Thr Asn Thr Trp Val His<br>385                       390                   395                   400 | 1200 | |
| agc aca aac atc ccc atc gac aag gaa gag gag aag cct gtg atg ctg<br>Ser Thr Asn Ile Pro Ile Asp Lys Glu Glu Glu Lys Pro Val Met Leu<br>                  405                   410                   415 | 1248 | |
| aaa att ggt acc tct ccc ctg aag gag gac aag gaa gca ttt gcc ata<br>Lys Ile Gly Thr Ser Pro Leu Lys Glu Asp Lys Glu Ala Phe Ala Ile<br>                420                   425                   430 | 1296 | |
| gtt cct gtt tcc cct gct gag gtt cgg gac ctg gac ttt gcc aat gat<br>Val Pro Val Ser Pro Ala Glu Val Arg Asp Leu Asp Phe Ala Asn Asp<br>435                       440                   445 | 1344 | |
| gcc agc aag gtg ctg ggc tcc atc gct ggg aag ttg gaa aag ggc acc<br>Ala Ser Lys Val Leu Gly Ser Ile Ala Gly Lys Leu Glu Lys Gly Thr<br>450                       455                   460 | 1392 | |
| atc acc cag aat gag aga agg tct gtc acg aag ctt ttg gaa gac ttg<br>Ile Thr Gln Asn Glu Arg Arg Ser Val Thr Lys Leu Leu Glu Asp Leu<br>465                       470                   475                   480 | 1440 | |
| gtt tac ttt gtc acg ggt gga act aac tct ggc caa gac gtg ctt gaa<br>Val Tyr Phe Val Thr Gly Gly Thr Asn Ser Gly Gln Asp Val Leu Glu<br>                  485                   490                   495 | 1488 | |
| gtt gtc ttc tct aag ccc aat cga gag cgg cag aag ctg atg agg gaa<br>Val Val Phe Ser Lys Pro Asn Arg Glu Arg Gln Lys Leu Met Arg Glu<br>                500                   505                   510 | 1536 | |
| cag aat att ctc aag cag atc ttc aag ctg ttg cag gcc ccc ttc acg<br>Gln Asn Ile Leu Lys Gln Ile Phe Lys Leu Leu Gln Ala Pro Phe Thr<br>                515                   520                   525 | 1584 | |
| gac tgc ggg gat ggc ccg atg ctt cgg ctg gag gag ctg ggg gat cag<br>Asp Cys Gly Asp Gly Pro Met Leu Arg Leu Glu Glu Leu Gly Asp Gln<br>                530                   535                   540 | 1632 | |
| cgc cat gct cct ttc aga cat att tgc cga ctc tgc tac agg gtc ctg<br>Arg His Ala Pro Phe Arg His Ile Cys Arg Leu Cys Tyr Arg Val Leu<br>545                       550                   555                   560 | 1680 | |
| cga cac tca cag caa gac tac agg aag aac cag gag tac ata gcc aag<br>Arg His Ser Gln Gln Asp Tyr Arg Lys Asn Gln Glu Tyr Ile Ala Lys<br>                  565                   570                   575 | 1728 | |

```
cag ttt ggc ttc atg cag aag cag att ggc tat gac gtg ctg gcc gaa    1776
Gln Phe Gly Phe Met Gln Lys Gln Ile Gly Tyr Asp Val Leu Ala Glu
            580                 585                 590 gac acc atc act gcc ctg ctc cac aac aac cgg aaa                    1812
Asp Thr Ile Thr Ala Leu Leu His Asn Asn Arg Lys
            595                 600
```

<210> SEQ ID NO 2
<211> LENGTH: 604
<212> TYPE: PRT
<213> ORGANISM: Mus musculus

<400> SEQUENCE: 2

```
Met Ser Asp Lys Met Ser Ser Phe Leu His Ile Gly Asp Ile Cys Ser
 1               5                  10                  15

Leu Tyr Ala Glu Gly Ser Thr Asn Gly Phe Ile Ser Thr Leu Gly Leu
            20                  25                  30

Val Asp Asp Arg Cys Val Val Gln Pro Glu Ala Gly Asp Leu Asn Asn
        35                  40                  45

Pro Pro Lys Lys Phe Arg Asp Cys Leu Phe Lys Leu Cys Pro Met Asn
    50                  55                  60

Arg Tyr Ser Ala Gln Lys Gln Phe Trp Lys Ala Ala Lys Pro Gly Ala
 65                  70                  75                  80

Asn Ser Thr Thr Asp Ala Val Leu Leu Asn Lys Leu His His Ala Ala
                85                  90                  95

Asp Leu Glu Lys Lys Gln Asn Glu Thr Glu Asn Arg Lys Leu Leu Gly
            100                 105                 110

Thr Val Ile Gln Tyr Gly Asn Val Ile Gln Leu Leu His Leu Lys Ser
        115                 120                 125

Asn Lys Tyr Leu Thr Val Asn Lys Arg Leu Pro Ala Leu Leu Glu Lys
    130                 135                 140

Asn Ala Met Arg Val Thr Leu Asp Glu Ala Gly Asn Glu Gly Ser Trp
145                 150                 155                 160

Phe Tyr Ile Gln Pro Phe Tyr Lys Leu Arg Ser Ile Gly Asp Ser Val
                165                 170                 175

Val Ile Gly Asp Lys Val Val Leu Asn Pro Val Asn Ala Gly Gln Pro
            180                 185                 190

Leu His Ala Ser Ser His Gln Leu Val Asp Asn Pro Gly Cys Asn Glu
        195                 200                 205

Val Asn Ser Val Asn Cys Asn Thr Ser Trp Lys Ile Val Leu Phe Met
    210                 215                 220

Lys Trp Ser Asp Asn Lys Asp Asp Ile Leu Lys Gly Gly Asp Val Val
225                 230                 235                 240

Arg Leu Phe His Ala Glu Gln Glu Lys Phe Leu Thr Cys Asp Glu His
                245                 250                 255

Arg Lys Lys Gln His Val Phe Leu Arg Thr Thr Gly Arg Gln Ser Ala
            260                 265                 270

Thr Ser Ala Thr Ser Ser Lys Ala Leu Trp Glu Val Glu Val Val Gln
        275                 280                 285

His Asp Pro Cys Arg Gly Gly Ala Gly Tyr Trp Asn Ser Leu Phe Arg
    290                 295                 300

Phe Lys His Leu Ala Thr Gly His Tyr Leu Ala Ala Glu Val Asp Pro
305                 310                 315                 320

Asp Phe Glu Glu Glu Cys Leu Glu Phe Gln Pro Ser Val Asp Pro Asp
                325                 330                 335
```

-continued

```
Gln Asp Ala Ser Arg Ser Arg Leu Arg Asn Ala Gln Glu Lys Met Val
            340                 345                 350
Tyr Ser Leu Val Ser Val Pro Glu Gly Asn Asp Ile Ser Ser Ile Phe
        355                 360                 365
Glu Leu Asp Pro Thr Thr Leu Arg Gly Gly Asp Ser Leu Val Pro Arg
    370                 375                 380
Asn Ser Tyr Val Arg Leu Arg His Leu Cys Thr Asn Thr Trp Val His
385                 390                 395                 400
Ser Thr Asn Ile Pro Ile Asp Lys Glu Glu Lys Pro Val Met Leu
                405                 410                 415
Lys Ile Gly Thr Ser Pro Leu Lys Glu Asp Lys Glu Ala Phe Ala Ile
            420                 425                 430
Val Pro Val Ser Pro Ala Glu Val Arg Asp Leu Asp Phe Ala Asn Asp
        435                 440                 445
Ala Ser Lys Val Leu Gly Ser Ile Ala Gly Lys Leu Glu Lys Gly Thr
    450                 455                 460
Ile Thr Gln Asn Glu Arg Arg Ser Val Thr Lys Leu Leu Glu Asp Leu
465                 470                 475                 480
Val Tyr Phe Val Thr Gly Gly Thr Asn Ser Gly Gln Asp Val Leu Glu
                485                 490                 495
Val Val Phe Ser Lys Pro Asn Arg Glu Arg Gln Lys Leu Met Arg Glu
            500                 505                 510
Gln Asn Ile Leu Lys Gln Ile Phe Lys Leu Leu Gln Ala Pro Phe Thr
        515                 520                 525
Asp Cys Gly Asp Gly Pro Met Leu Arg Leu Glu Glu Leu Gly Asp Gln
    530                 535                 540
Arg His Ala Pro Phe Arg His Ile Cys Arg Leu Cys Tyr Arg Val Leu
545                 550                 555                 560
Arg His Ser Gln Gln Asp Tyr Arg Lys Asn Gln Glu Tyr Ile Ala Lys
                565                 570                 575
Gln Phe Gly Phe Met Gln Lys Gln Ile Gly Tyr Asp Val Leu Ala Glu
            580                 585                 590
Asp Thr Ile Thr Ala Leu Leu His Asn Asn Arg Lys
        595                 600

<210> SEQ ID NO 3
<211> LENGTH: 9848
<212> TYPE: DNA
<213> ORGANISM: Mus musculus
<220> FEATURE:
<221> NAME/KEY: CDS
<222> LOCATION: (329)..(8575)

<400> SEQUENCE: 3
gctgaagcgt tcctcaagc ctgccggggt gggaggagag gaggaggtgg tggtggtgga      60
ggaggtggag gcagagggtg gagagagaga aagcgcacgc cgagaggagg tgtgggtgtt    120
ccgctcccat cctaacggaa cgagctccct cttcgcggac atgggattgc ccagcggctg    180
ctaacccctc tcctggtcct gatccccaa accggcgtgg ctccccggtc accaaggagc    240
tgattacaag ggaccaggat ttgcatcctt ggctggcgt ccattggcta cagagtgcct    300
gacctgggtc aggctttcca acacggac atg tct gac aaa atg tcg agt ttc       352
                              Met Ser Asp Lys Met Ser Ser Phe
                                  1               5 cta cat att gga gac att tgt tct ctg tat gcg gag gga tct acg aat      400
Leu His Ile Gly Asp Ile Cys Ser Leu Tyr Ala Glu Gly Ser Thr Asn
```

-continued

```
                 10                    15                    20
gga ttt atc agc acc tta ggc ttg gtt gat gac cgt tgt gtt gta cag        448
Gly Phe Ile Ser Thr Leu Gly Leu Val Asp Asp Arg Cys Val Val Gln
 25                   30                    35                    40 cca gaa gcc ggg gac ctt aac aat cca ccc aag aaa ttc aga gac tgc        496
Pro Glu Ala Gly Asp Leu Asn Asn Pro Pro Lys Lys Phe Arg Asp Cys
                      45                    50                    55 ctc ttt aag cta tgt cct atg aat cga tac tcc gca cag aaa cag ttc        544
Leu Phe Lys Leu Cys Pro Met Asn Arg Tyr Ser Ala Gln Lys Gln Phe
                 60                    65                    70 tgg aaa gct gct aag ccc ggg gcc aac agc act aca gat gca gtg ctg        592
Trp Lys Ala Ala Lys Pro Gly Ala Asn Ser Thr Thr Asp Ala Val Leu
             75                    80                    85 ctc aac aaa ttg cat cat gct gca gac ttg gaa aag aag cag aat gag        640
Leu Asn Lys Leu His His Ala Ala Asp Leu Glu Lys Lys Gln Asn Glu
         90                    95                   100 aca gaa aac agg aaa ttg ttg ggg acc gtc atc caa tat ggc aac gtg        688
Thr Glu Asn Arg Lys Leu Leu Gly Thr Val Ile Gln Tyr Gly Asn Val
105                   110                   115                   120 atc cag ctc ctg cat ttg aaa agc aat aaa tac ctg act gtg aat aag        736
Ile Gln Leu Leu His Leu Lys Ser Asn Lys Tyr Leu Thr Val Asn Lys
                      125                   130                   135 agg ctc cca gcc ttg cta gag aag aat gcc atg agg gtg acg ttg gac        784
Arg Leu Pro Ala Leu Leu Glu Lys Asn Ala Met Arg Val Thr Leu Asp
                 140                   145                   150 gag gct gga aat gaa ggg tcc tgg ttt tac att caa cca ttt tac aag        832
Glu Ala Gly Asn Glu Gly Ser Trp Phe Tyr Ile Gln Pro Phe Tyr Lys
             155                   160                   165 ctt cgc tcc atc gga gac agt gtg gtc ata ggc gac aag gta gtt ttg        880
Leu Arg Ser Ile Gly Asp Ser Val Val Ile Gly Asp Lys Val Val Leu
         170                   175                   180 aat cct gtc aat gct ggc cag cct cta cat gcc agc agt cat cag ctg        928
Asn Pro Val Asn Ala Gly Gln Pro Leu His Ala Ser Ser His Gln Leu
185                   190                   195                   200 gtg gat aac cca ggc tgc aat gag gtc aac tcc gtc aac tgt aat aca        976
Val Asp Asn Pro Gly Cys Asn Glu Val Asn Ser Val Asn Cys Asn Thr
                      205                   210                   215 agc tgg aag ata gtg ctt ttc atg aaa tgg agt gat aac aaa gac gac       1024
Ser Trp Lys Ile Val Leu Phe Met Lys Trp Ser Asp Asn Lys Asp Asp
                 220                   225                   230 att ctc aaa gga ggt gat gtg gtg agg ctc ttc cat gcc gag caa gag       1072
Ile Leu Lys Gly Gly Asp Val Val Arg Leu Phe His Ala Glu Gln Glu
             235                   240                   245 aag ttt ctc acc tgt gat gag cac cgg aag aag cag cat gtg ttc ctg       1120
Lys Phe Leu Thr Cys Asp Glu His Arg Lys Lys Gln His Val Phe Leu
         250                   255                   260 agg acc acc ggc agg cag tca gcc acg tcg gcc acc agt tct aaa gcc       1168
Arg Thr Thr Gly Arg Gln Ser Ala Thr Ser Ala Thr Ser Ser Lys Ala
265                   270                   275                   280 ctg tgg gaa gtg gag gta gtc cag cac gac cca tgt cgg ggt gga gct       1216
Leu Trp Glu Val Glu Val Val Gln His Asp Pro Cys Arg Gly Gly Ala
                      285                   290                   295 ggg tac tgg aat agc ctc ttc cgg ttc aag cac ctg gct aca ggg cat       1264
Gly Tyr Trp Asn Ser Leu Phe Arg Phe Lys His Leu Ala Thr Gly His
                 300                   305                   310 tac ttg gct gca gag gta gac cct gac ttt gag gaa gaa tgc ctg gag       1312
Tyr Leu Ala Ala Glu Val Asp Pro Asp Phe Glu Glu Glu Cys Leu Glu
             315                   320                   325 ttt cag ccc tca gtg gac cct gat cag gat gca tct cgg agt agg ttg       1360
```

-continued

```
                Phe Gln Pro Ser Val Asp Pro Asp Gln Asp Ala Ser Arg Ser Arg Leu
                    330                 335                 340 aga aac gcg caa gaa aaa atg gta tac tct ctg gtc tcc gtg cct gaa        1408
Arg Asn Ala Gln Glu Lys Met Val Tyr Ser Leu Val Ser Val Pro Glu
345                 350                 355                 360 ggc aac gac atc tcc tcc atc ttt gag cta gac ccc acg act ctg cgt        1456
Gly Asn Asp Ile Ser Ser Ile Phe Glu Leu Asp Pro Thr Thr Leu Arg
                365                 370                 375 gga ggt gac agc ctt gtc cca agg aac tcc tat gtc cgt ctc aga cac        1504
Gly Gly Asp Ser Leu Val Pro Arg Asn Ser Tyr Val Arg Leu Arg His
            380                 385                 390 ctg tgc acc aac acc tgg gta cac agc aca aac atc ccc atc gac aag        1552
Leu Cys Thr Asn Thr Trp Val His Ser Thr Asn Ile Pro Ile Asp Lys
        395                 400                 405 gaa gag gag aag cct gtg atg ctg aaa att ggt acc tct ccc ctg aag        1600
Glu Glu Glu Lys Pro Val Met Leu Lys Ile Gly Thr Ser Pro Leu Lys
    410                 415                 420 gag gac aag gaa gca ttt gcc ata gtt cct gtt tcc cct gct gag gtt        1648
Glu Asp Lys Glu Ala Phe Ala Ile Val Pro Val Ser Pro Ala Glu Val
425                 430                 435                 440 cgg gac ctg gac ttt gcc aat gat gcc agc aag gtg ctg ggc tcc atc        1696
Arg Asp Leu Asp Phe Ala Asn Asp Ala Ser Lys Val Leu Gly Ser Ile
                445                 450                 455 gct ggg aag ttg gaa aag ggc acc atc acc cag aat gag aga agg tct        1744
Ala Gly Lys Leu Glu Lys Gly Thr Ile Thr Gln Asn Glu Arg Arg Ser
            460                 465                 470 gtc acg aag ctt ttg gaa gac ttg gtt tac ttt gtc acg ggt gga act        1792
Val Thr Lys Leu Leu Glu Asp Leu Val Tyr Phe Val Thr Gly Gly Thr
        475                 480                 485 aac tct ggc caa gac gtg ctt gaa gtt gtc ttc tct aag ccc aat cga        1840
Asn Ser Gly Gln Asp Val Leu Glu Val Val Phe Ser Lys Pro Asn Arg
    490                 495                 500 gag cgg cag aag ctg atg agg gaa cag aat att ctc aag cag atc ttc        1888
Glu Arg Gln Lys Leu Met Arg Glu Gln Asn Ile Leu Lys Gln Ile Phe
505                 510                 515                 520 aag ctg ttg cag gcc ccc ttc acg gac tgc ggg gat ggc ccg atg ctt        1936
Lys Leu Leu Gln Ala Pro Phe Thr Asp Cys Gly Asp Gly Pro Met Leu
                525                 530                 535 cgg ctg gag gag ctg ggg gat cag cgc cat gct cct ttc aga cat att        1984
Arg Leu Glu Glu Leu Gly Asp Gln Arg His Ala Pro Phe Arg His Ile
            540                 545                 550 tgc cga ctc tgc tac agg gtc ctg cga cac tca cag caa gac tac agg        2032
Cys Arg Leu Cys Tyr Arg Val Leu Arg His Ser Gln Gln Asp Tyr Arg
        555                 560                 565 aag aac cag gag tac ata gcc aag cag ttt ggc ttc atg cag aag cag        2080
Lys Asn Gln Glu Tyr Ile Ala Lys Gln Phe Gly Phe Met Gln Lys Gln
    570                 575                 580 att ggc tat gac gtg ctg gcc gaa gac acc atc act gcc ctg ctc cac        2128
Ile Gly Tyr Asp Val Leu Ala Glu Asp Thr Ile Thr Ala Leu Leu His
585                 590                 595                 600 aac aac cgg aaa ctc ctg gag aag cac atc acc gcg gca gag att gac        2176
Asn Asn Arg Lys Leu Leu Glu Lys His Ile Thr Ala Ala Glu Ile Asp
                605                 610                 615 acg ttt gtc agc ctg gtg cga aag aac agg gag ccc agg ttc ttg gat        2224
Thr Phe Val Ser Leu Val Arg Lys Asn Arg Glu Pro Arg Phe Leu Asp
            620                 625                 630 tac ctc tct gac ctc tgc gta tcc atg aac aag tca atc cct gtg aca        2272
Tyr Leu Ser Asp Leu Cys Val Ser Met Asn Lys Ser Ile Pro Val Thr
        635                 640                 645
```

```
                                              -continued cag gag ctc atc tgt aaa gct gtg ctc aat ccc acc aat gct gac atc        2320
Gln Glu Leu Ile Cys Lys Ala Val Leu Asn Pro Thr Asn Ala Asp Ile
        650                 655                 660 ctg att gag acc aag ctg gtt ctt tct cgt ttt gag ttt gaa ggc gtt        2368
Leu Ile Glu Thr Lys Leu Val Leu Ser Arg Phe Glu Phe Glu Gly Val
665                 670                 675                 680 tcc act gga gag aat gct ctg gaa gcc ggg gag gat gag gaa gag gtg        2416
Ser Thr Gly Glu Asn Ala Leu Glu Ala Gly Glu Asp Glu Glu Glu Val
                685                 690                 695 tgg ctg ttc tgg agg gac agc aac aaa gag atc cgt agt aag agt gtc        2464
Trp Leu Phe Trp Arg Asp Ser Asn Lys Glu Ile Arg Ser Lys Ser Val
            700                 705                 710 cgg gaa ttg gcg caa gat gct aaa gag gga cag aag gaa gac agg gac        2512
Arg Glu Leu Ala Gln Asp Ala Lys Glu Gly Gln Lys Glu Asp Arg Asp
        715                 720                 725 atc ctc agc tac tac aga tat cag ctg aac ctc ttt gca agg atg tgt        2560
Ile Leu Ser Tyr Tyr Arg Tyr Gln Leu Asn Leu Phe Ala Arg Met Cys
    730                 735                 740 ctg gac cgc cag tac ctg gcc atc aat gaa atc tcc ggg cag ctg gat        2608
Leu Asp Arg Gln Tyr Leu Ala Ile Asn Glu Ile Ser Gly Gln Leu Asp
745                 750                 755                 760 gtt gat ctc att ctc cgc tgc atg tct gac gag aac ctc ccc tac gac        2656
Val Asp Leu Ile Leu Arg Cys Met Ser Asp Glu Asn Leu Pro Tyr Asp
                765                 770                 775 ctc agg gca tcc ttt tgc cgc ctc atg ctt cac atg cat gtg gac cga        2704
Leu Arg Ala Ser Phe Cys Arg Leu Met Leu His Met His Val Asp Arg
            780                 785                 790 gat ccc caa gag cag gtg aca cct gtg aaa tat gcc cga ctg tgg tca        2752
Asp Pro Gln Glu Gln Val Thr Pro Val Lys Tyr Ala Arg Leu Trp Ser
        795                 800                 805 gaa att ccc tct gag atc gcc att gat gac tat gac agc agt gga aca        2800
Glu Ile Pro Ser Glu Ile Ala Ile Asp Asp Tyr Asp Ser Ser Gly Thr
    810                 815                 820 tcc aaa gat gaa att aag gag agg ttt gca cag acg atg gag ttt gtg        2848
Ser Lys Asp Glu Ile Lys Glu Arg Phe Ala Gln Thr Met Glu Phe Val
825                 830                 835                 840 gag gag tac cta aga gat gtg gtt tgt caa aga ttc ccc ttc tct gat        2896
Glu Glu Tyr Leu Arg Asp Val Val Cys Gln Arg Phe Pro Phe Ser Asp
                845                 850                 855 aag gag aaa aat aag ctc acg ttt gag gtt gtg aac tta gcc agg aat        2944
Lys Glu Lys Asn Lys Leu Thr Phe Glu Val Val Asn Leu Ala Arg Asn
            860                 865                 870 ctc ata tac ttt ggt ttc tac aac ttt tct gac ctt ctc cga tta acc        2992
Leu Ile Tyr Phe Gly Phe Tyr Asn Phe Ser Asp Leu Leu Arg Leu Thr
        875                 880                 885 aag atc ctc ttg gca atc tta gac tgt gtc cat gtg acc act atc ttc        3040
Lys Ile Leu Leu Ala Ile Leu Asp Cys Val His Val Thr Thr Ile Phe
    890                 895                 900 ccc att agc aag atg aca aaa gga gaa gag aat aaa ggc agt aac gtg        3088
Pro Ile Ser Lys Met Thr Lys Gly Glu Glu Asn Lys Gly Ser Asn Val
905                 910                 915                 920 atg agg tct atc cat ggc gtt ggg gag ctg atg acc cag gtg gtg ctg        3136
Met Arg Ser Ile His Gly Val Gly Glu Leu Met Thr Gln Val Val Leu
                925                 930                 935 cgg gga gga ggc ttc ttg ccc atg act ccc atg gct gcg gcc cct gaa        3184
Arg Gly Gly Gly Phe Leu Pro Met Thr Pro Met Ala Ala Ala Pro Glu
            940                 945                 950 gga aat gtg aag cag gca gag cca gag aaa gag gac atc atg gtc atg        3232
Gly Asn Val Lys Gln Ala Glu Pro Glu Lys Glu Asp Ile Met Val Met
        955                 960                 965
```

-continued

| | |
|---|---|
| gac acc aag ttg aag atc att gaa ata ctc cag ttt att ttg aat gtg<br>Asp Thr Lys Leu Lys Ile Ile Glu Ile Leu Gln Phe Ile Leu Asn Val<br>970                        975                  980 | 3280 |
| aga ttg gat tat agg atc tcc tgc ctc ctg tgt ata ttt aag cga gag<br>Arg Leu Asp Tyr Arg Ile Ser Cys Leu Leu Cys Ile Phe Lys Arg Glu<br>985                        990                  995              1000 | 3328 |
| ttt gat gaa agc aat tcc cag tca tca gaa aca tcc tcc gga aac agc<br>Phe Asp Glu Ser Asn Ser Gln Ser Ser Glu Thr Ser Ser Gly Asn Ser<br>1005                    1010                  1015 | 3376 |
| agc cag gaa ggg cca agt aat gtg cca ggt gct ctt gac ttt gaa cac<br>Ser Gln Glu Gly Pro Ser Asn Val Pro Gly Ala Leu Asp Phe Glu His<br>1020                    1025                  1030 | 3424 |
| att gaa gaa caa gcg gaa ggc atc ttt gga gga agt gag gag aac aca<br>Ile Glu Glu Gln Ala Glu Gly Ile Phe Gly Gly Ser Glu Glu Asn Thr<br>1035                    1040                  1045 | 3472 |
| cct ttg gac ctg gat gac cat ggt ggc aga acc ttc ctc agg gtc ctg<br>Pro Leu Asp Leu Asp Asp His Gly Gly Arg Thr Phe Leu Arg Val Leu<br>1050                    1055                  1060 | 3520 |
| ctc cac ttg aca atg cat gac tac cca ccc ctg gtg tct ggg gcc ctg<br>Leu His Leu Thr Met His Asp Tyr Pro Pro Leu Val Ser Gly Ala Leu<br>1065                    1070                  1075                  1080 | 3568 |
| cag ctc ctc ttt cgg cac ttc agc cag agg cag gag gtc ctt cag gcc<br>Gln Leu Leu Phe Arg His Phe Ser Gln Arg Gln Glu Val Leu Gln Ala<br>1085                    1090                  1095 | 3616 |
| ttc aaa cag gtt caa ctg ctg gtt act agc caa gat gtg gac aac tac<br>Phe Lys Gln Val Gln Leu Leu Val Thr Ser Gln Asp Val Asp Asn Tyr<br>1100                    1105                  1110 | 3664 |
| aaa cag atc aag caa gac ttg gac caa cta agg tcc att gtg gag aag<br>Lys Gln Ile Lys Gln Asp Leu Asp Gln Leu Arg Ser Ile Val Glu Lys<br>1115                    1120                  1125 | 3712 |
| tct gag ctc tgg gtg tac aaa ggc caa ggt ccc gat gag cct atg gac<br>Ser Glu Leu Trp Val Tyr Lys Gly Gln Gly Pro Asp Glu Pro Met Asp<br>1130                    1135                  1140 | 3760 |
| gga gcc tcc ggt gaa aat gag cat aag aaa acc gag gag ggg acg agc<br>Gly Ala Ser Gly Glu Asn Glu His Lys Lys Thr Glu Glu Gly Thr Ser<br>1145                    1150                  1155                  1160 | 3808 |
| aag cca ctg aag cac gag agc acc agc agc tac aac tac cga gtg gtg<br>Lys Pro Leu Lys His Glu Ser Thr Ser Ser Tyr Asn Tyr Arg Val Val<br>1165                    1170                  1175 | 3856 |
| aaa gag att ttg att cga ctt agc aag ctc tgc gtg cag gag agc gcg<br>Lys Glu Ile Leu Ile Arg Leu Ser Lys Leu Cys Val Gln Glu Ser Ala<br>1180                    1185                  1190 | 3904 |
| tcg gtg agg aag agc cgg aag cag cag caa cga ctg ctg agg aac atg<br>Ser Val Arg Lys Ser Arg Lys Gln Gln Gln Arg Leu Leu Arg Asn Met<br>1195                    1200                  1205 | 3952 |
| ggc gca cac gct gtg gtg ctg gag ctg ctg cag atc ccc tac gag aag<br>Gly Ala His Ala Val Val Leu Glu Leu Leu Gln Ile Pro Tyr Glu Lys<br>1210                    1215                  1220 | 4000 |
| gcc gaa gac aca aag atg caa gag atc atg cgg ctg gct cat gaa ttt<br>Ala Glu Asp Thr Lys Met Gln Glu Ile Met Arg Leu Ala His Glu Phe<br>1225                    1230                  1235                  1240 | 4048 |
| ttg cag aat ttc tgt gca ggc aac cag cag aat caa gct ttg ctg cat<br>Leu Gln Asn Phe Cys Ala Gly Asn Gln Gln Asn Gln Ala Leu Leu His<br>1245                    1250                  1255 | 4096 |
| aaa cac ata aac ctg ttt ctc aag cca ggg atc ctg gag gca gtg acg<br>Lys His Ile Asn Leu Phe Leu Lys Pro Gly Ile Leu Glu Ala Val Thr<br>1260                    1265                  1270 | 4144 |
| atg cag cac atc ttc atg aac aac ttc cag ctg tgc agt gag atc aac<br>Met Gln His Ile Phe Met Asn Asn Phe Gln Leu Cys Ser Glu Ile Asn | 4192 |

-continued

```
            1275                1280                1285
gag aga gtg gtc cag cac ttt gtt cac tgc ata gag acc cac ggt cga    4240
Glu Arg Val Val Gln His Phe Val His Cys Ile Glu Thr His Gly Arg
    1290                1295                1300 aac gtc cag tat atc aag ttt ctc cag acg att gtc aag gca gaa ggg    4288
Asn Val Gln Tyr Ile Lys Phe Leu Gln Thr Ile Val Lys Ala Glu Gly
1305                1310                1315                1320 aaa ttc att aaa aag tgc caa gac atg gtc atg gct gag ctt gtc aac    4336
Lys Phe Ile Lys Lys Cys Gln Asp Met Val Met Ala Glu Leu Val Asn
            1325                1330                1335 tct gga gag gac gtc ctc gtg ttc tac aat gac aga gcc tct ttc cag    4384
Ser Gly Glu Asp Val Leu Val Phe Tyr Asn Asp Arg Ala Ser Phe Gln
        1340                1345                1350 act ctg atc cag atg atg cgg tcc gag cgt gac cgg atg gat gag aac    4432
Thr Leu Ile Gln Met Met Arg Ser Glu Arg Asp Arg Met Asp Glu Asn
    1355                1360                1365 agc cct ctc atg tac cac atc cat ctg gtg gag ctc ttg gcc gtg tgc    4480
Ser Pro Leu Met Tyr His Ile His Leu Val Glu Leu Leu Ala Val Cys
1370                1375                1380 aca gag ggc aag aat gtg tac acg gag atc aag tgc aac tcc ttg ctc    4528
Thr Glu Gly Lys Asn Val Tyr Thr Glu Ile Lys Cys Asn Ser Leu Leu
1385                1390                1395                1400 ccg ctc gat gac atc gtt cgt gtg gtc act cat gaa gac tgc atc ccc    4576
Pro Leu Asp Asp Ile Val Arg Val Val Thr His Glu Asp Cys Ile Pro
            1405                1410                1415 gag gtt aag atc gct tac att aac ttc ctg aat cac tgc tat gtg gat    4624
Glu Val Lys Ile Ala Tyr Ile Asn Phe Leu Asn His Cys Tyr Val Asp
        1420                1425                1430 acg gag gtg gag atg aag gag att tac aca agc aac cac atg tgg aag    4672
Thr Glu Val Glu Met Lys Glu Ile Tyr Thr Ser Asn His Met Trp Lys
    1435                1440                1445 ttg ttt gag aat ttc ctc gtg gac atc tgc agg gcc tgt aac aac aca    4720
Leu Phe Glu Asn Phe Leu Val Asp Ile Cys Arg Ala Cys Asn Asn Thr
1450                1455                1460 agc gac agg aag cac gca gac tcc att ctg gag aag tac gtc act gaa    4768
Ser Asp Arg Lys His Ala Asp Ser Ile Leu Glu Lys Tyr Val Thr Glu
1465                1470                1475                1480 atc gtg atg agc atc gtc acc acc ttc ttc agc tct ccc ttc tca gac    4816
Ile Val Met Ser Ile Val Thr Thr Phe Phe Ser Ser Pro Phe Ser Asp
            1485                1490                1495 cag agc acc act ctg cag acc cgc cag cct gtc ttt gtg caa ctc ctg    4864
Gln Ser Thr Thr Leu Gln Thr Arg Gln Pro Val Phe Val Gln Leu Leu
        1500                1505                1510 caa ggc gtg ttc cga gtt tac cac tgc aac tgg ctg atg ccg agc caa    4912
Gln Gly Val Phe Arg Val Tyr His Cys Asn Trp Leu Met Pro Ser Gln
    1515                1520                1525 aaa gcc tcg gtg gag agc tgc atc cgg gtg ctc tct gac gta gcc aag    4960
Lys Ala Ser Val Glu Ser Cys Ile Arg Val Leu Ser Asp Val Ala Lys
1530                1535                1540 agc cgg gcc ata gcc att cct gtt gac ctg gac agc caa gtc aac aac    5008
Ser Arg Ala Ile Ala Ile Pro Val Asp Leu Asp Ser Gln Val Asn Asn
1545                1550                1555                1560 ctc ttc ctg aag tcc cac aac att gtg cag aaa aca gcc ctg aac tgg    5056
Leu Phe Leu Lys Ser His Asn Ile Val Gln Lys Thr Ala Leu Asn Trp
            1565                1570                1575 cgg tta tca gcc cga aac gcc gct cgc aga gac tct gta ctg gca gca    5104
Arg Leu Ser Ala Arg Asn Ala Ala Arg Arg Asp Ser Val Leu Ala Ala
        1580                1585                1590 tcc aga gac tac cga aat atc att gag agg tta cag gac atc gtg tct    5152
```

```
Ser Arg Asp Tyr Arg Asn Ile Ile Glu Arg Leu Gln Asp Ile Val Ser
             1595                1600                1605 gcc cta gag gac cgg ctc agg ccc ctg gtg cag gct gag ctg tct gtg      5200
Ala Leu Glu Asp Arg Leu Arg Pro Leu Val Gln Ala Glu Leu Ser Val
1610                1615                1620 ctc gtg gat gtt cta cac aga cca gaa ctg ctc ttc ccc gag aac acg      5248
Leu Val Asp Val Leu His Arg Pro Glu Leu Leu Phe Pro Glu Asn Thr
1625                1630                1635                1640 gat gcc agg agg aaa tgt gag agt gga ggt ttc atc tgc aag cta ata      5296
Asp Ala Arg Arg Lys Cys Glu Ser Gly Gly Phe Ile Cys Lys Leu Ile
             1645                1650                1655 aaa cat acc aag caa ctg ctg gag gag aat gaa gag aaa cta tgc att      5344
Lys His Thr Lys Gln Leu Leu Glu Glu Asn Glu Glu Lys Leu Cys Ile
         1660                1665                1670 aaa gtc tta cag acc ctc agg gaa atg atg acc aaa gac aga ggc tat      5392
Lys Val Leu Gln Thr Leu Arg Glu Met Met Thr Lys Asp Arg Gly Tyr
    1675                1680                1685 gga gag aag caa att tcc att gat gaa tcg gaa aat gcc gag ctg cca      5440
Gly Glu Lys Gln Ile Ser Ile Asp Glu Ser Glu Asn Ala Glu Leu Pro
1690                1695                1700 cag gca ccg gaa gct gag aac tcc aca gag cag gag ctt gaa cca agt      5488
Gln Ala Pro Glu Ala Glu Asn Ser Thr Glu Gln Glu Leu Glu Pro Ser
1705                1710                1715                1720 cca ccc ctg agg caa ctg gaa gac cat aaa agg ggt gag gca ctc cga      5536
Pro Pro Leu Arg Gln Leu Glu Asp His Lys Arg Gly Glu Ala Leu Arg
             1725                1730                1735 caa att ttg gtc aac cgt tac tat gga aac atc aga cct tca gga aga      5584
Gln Ile Leu Val Asn Arg Tyr Tyr Gly Asn Ile Arg Pro Ser Gly Arg
         1740                1745                1750 aga gag agc ctt acc agc ttt ggc aat ggc cca cta tca cca gga gga      5632
Arg Glu Ser Leu Thr Ser Phe Gly Asn Gly Pro Leu Ser Pro Gly Gly
    1755                1760                1765 ccc agc aag cct ggt gga gga ggg gga ggt cct gga tct agt tcc aca      5680
Pro Ser Lys Pro Gly Gly Gly Gly Gly Pro Gly Ser Ser Ser Thr
 1770                1775                1780 agc agg ggt gag atg agc ctg gct gag gtt cag tgt cac ctc gac aag      5728
Ser Arg Gly Glu Met Ser Leu Ala Glu Val Gln Cys His Leu Asp Lys
1785                1790                1795                1800 gag ggg gcc tcc aac ctg gtc atc gat ctc ata atg aat gca tcc agt      5776
Glu Gly Ala Ser Asn Leu Val Ile Asp Leu Ile Met Asn Ala Ser Ser
             1805                1810                1815 gac cga gta ttc cat gaa agc att ctg ctg gcc atc gca ctt ctg gaa      5824
Asp Arg Val Phe His Glu Ser Ile Leu Leu Ala Ile Ala Leu Leu Glu
         1820                1825                1830 gga ggc aac acc acc atc cag cac tcg ttt ttc tgc cgg ctg aca gaa      5872
Gly Gly Asn Thr Thr Ile Gln His Ser Phe Phe Cys Arg Leu Thr Glu
    1835                1840                1845 gat aag aaa tca gag aag ttc ttc aag gtt ttt tac gat cga atg aag      5920
Asp Lys Lys Ser Glu Lys Phe Phe Lys Val Phe Tyr Asp Arg Met Lys
1850                1855                1860 gtg gcc cag cag gaa atc aag gcg aca gtg aca gtg aac acc agc gac      5968
Val Ala Gln Gln Glu Ile Lys Ala Thr Val Thr Val Asn Thr Ser Asp
1865                1870                1875                1880 ttg gga aac aaa aag aaa gat gat gaa gtg gac agg gat gcc ccg tct      6016
Leu Gly Asn Lys Lys Lys Asp Asp Glu Val Asp Arg Asp Ala Pro Ser
             1885                1890                1895 cgg aag aaa gcc aaa gag ccc aca aca cag ata aca gaa gag gtc cgg      6064
Arg Lys Lys Ala Lys Glu Pro Thr Thr Gln Ile Thr Glu Glu Val Arg
         1900                1905                1910
```

-continued

| | |
|---|---|
| gat cag ctc ctg gaa gca tct gct gcc acc agg aaa gcc ttt acc acc<br>Asp Gln Leu Leu Glu Ala Ser Ala Ala Thr Arg Lys Ala Phe Thr Thr<br>     1915                 1920                1925 | 6112 |
| ttc cgg agg gag gcc gac cct gat gac cat tac cag tct ggg gag ggc<br>Phe Arg Arg Glu Ala Asp Pro Asp Asp His Tyr Gln Ser Gly Glu Gly<br>     1930                 1935                1940 | 6160 |
| acc cag gct aca acc gac aaa gcc aag gat gac cta gag atg agc gct<br>Thr Gln Ala Thr Thr Asp Lys Ala Lys Asp Asp Leu Glu Met Ser Ala<br>1945               1950                1955                1960 | 6208 |
| gtc atc acc atc atg cag cct atc ctg cgc ttc ctg cag ctg ctg tgt<br>Val Ile Thr Ile Met Gln Pro Ile Leu Arg Phe Leu Gln Leu Leu Cys<br>     1965                 1970                1975 | 6256 |
| gaa aac cac aac cga gat ctg cag aat ttc ctt cgt tgc caa aat aat<br>Glu Asn His Asn Arg Asp Leu Gln Asn Phe Leu Arg Cys Gln Asn Asn<br>              1980                1985                1990 | 6304 |
| aag acc aac tac aat ttg gtg tgt gag aca ctg cag ttt ctg gac tgt<br>Lys Thr Asn Tyr Asn Leu Val Cys Glu Thr Leu Gln Phe Leu Asp Cys<br>     1995                 2000                2005 | 6352 |
| att tgt ggg agc aca acc gga ggc ctt ggt ctt ctt gga ctg tac ata<br>Ile Cys Gly Ser Thr Thr Gly Gly Leu Gly Leu Leu Gly Leu Tyr Ile<br>     2010                 2015                2020 | 6400 |
| aat gaa aag aat gta gca ctt atc aac caa acc ctg gag agt ctg acg<br>Asn Glu Lys Asn Val Ala Leu Ile Asn Gln Thr Leu Glu Ser Leu Thr<br>2025               2030                2035                2040 | 6448 |
| gag tac tgt caa ggg cct tgc cat gag aac cag aac tgc atc gcc acc<br>Glu Tyr Cys Gln Gly Pro Cys His Glu Asn Gln Asn Cys Ile Ala Thr<br>              2045                2050                2055 | 6496 |
| cac gag tcc aat ggc atc gat atc atc aca gcc ctc atc ctc aat gat<br>His Glu Ser Asn Gly Ile Asp Ile Ile Thr Ala Leu Ile Leu Asn Asp<br>     2060                 2065                2070 | 6544 |
| atc aac cct ctg gga aag aag cgg atg gac ctg gtg tta gaa ctg aag<br>Ile Asn Pro Leu Gly Lys Lys Arg Met Asp Leu Val Leu Glu Leu Lys<br>2075               2080                2085 | 6592 |
| aac aat gct tcg aag ctg cta ctg gcc atc atg gaa agc aga cac gat<br>Asn Asn Ala Ser Lys Leu Leu Leu Ala Ile Met Glu Ser Arg His Asp<br>     2090                 2095                2100 | 6640 |
| agt gaa aat gca gag agg atc ctg tac aac atg agg ccc aag gag ctg<br>Ser Glu Asn Ala Glu Arg Ile Leu Tyr Asn Met Arg Pro Lys Glu Leu<br>2105               2110                2115                2120 | 6688 |
| gtg gaa gtg atc aag aag gcc tac atg caa ggt gaa gtg gaa ttt gag<br>Val Glu Val Ile Lys Lys Ala Tyr Met Gln Gly Glu Val Glu Phe Glu<br>              2125                2130                2135 | 6736 |
| gat ggg gag aac ggt gag gat gga gct gcc tca ccc agg aac gtg ggc<br>Asp Gly Glu Asn Gly Glu Asp Gly Ala Ala Ser Pro Arg Asn Val Gly<br>     2140                 2145                2150 | 6784 |
| cac aac atc tac atc ctc gct cac cag ttg gct cgg cat aac aaa gaa<br>His Asn Ile Tyr Ile Leu Ala His Gln Leu Ala Arg His Asn Lys Glu<br>2155               2160                2165 | 6832 |
| ctt caa acc atg ctg aaa cct gga ggc cag gtg gat ggg gat gaa gct<br>Leu Gln Thr Met Leu Lys Pro Gly Gly Gln Val Asp Gly Asp Glu Ala<br>     2170                 2175                2180 | 6880 |
| ctg gag ttc tac gcg aag cac aca gca caa att gag att gtc aga ctg<br>Leu Glu Phe Tyr Ala Lys His Thr Ala Gln Ile Glu Ile Val Arg Leu<br>2185               2190                2195                2200 | 6928 |
| gac cgg aca atg gaa cag atc gtc ttc cct gtg ccc agc atc tgt gaa<br>Asp Arg Thr Met Glu Gln Ile Val Phe Pro Val Pro Ser Ile Cys Glu<br>              2205                2210                2215 | 6976 |
| ttc ctg act aag gaa tcg aaa ctt cga ata tat tac acc aca gag cgg<br>Phe Leu Thr Lys Glu Ser Lys Leu Arg Ile Tyr Tyr Thr Thr Glu Arg<br>     2220                 2225                2230 | 7024 |

-continued

```
gat gag caa ggt agc aag atc aat gac ttc ttc ctg cgc tcc gag gac      7072
Asp Glu Gln Gly Ser Lys Ile Asn Asp Phe Phe Leu Arg Ser Glu Asp
            2235                2240                2245 ctc ttt aac gag atg aac tgg cag aag aaa ctt cga gcc cag cct gtc      7120
Leu Phe Asn Glu Met Asn Trp Gln Lys Lys Leu Arg Ala Gln Pro Val
2250                2255                2260 ttg tac tgg tgt gcc cga aac atg tct ttc tgg agc agc atc tcc ttc      7168
Leu Tyr Trp Cys Ala Arg Asn Met Ser Phe Trp Ser Ser Ile Ser Phe
2265                2270                2275                2280 aac ctg gcc gtc ctg atg aac ctg ctg gtg gcg ttt ttc tat cca ttt      7216
Asn Leu Ala Val Leu Met Asn Leu Leu Val Ala Phe Phe Tyr Pro Phe
                2285                2290                2295 aaa gga gtg agg gga gga aca cta gag cca cac tgg tca ggc ctc ctg      7264
Lys Gly Val Arg Gly Gly Thr Leu Glu Pro His Trp Ser Gly Leu Leu
            2300                2305                2310 tgg aca gcc atg ctc atc tct ctg gcc att gtc att gct ctg ccc aag      7312
Trp Thr Ala Met Leu Ile Ser Leu Ala Ile Val Ile Ala Leu Pro Lys
        2315                2320                2325 ccc cac ggc atc cgg gcc tta att gct tct aca atc cta cga ctg ata      7360
Pro His Gly Ile Arg Ala Leu Ile Ala Ser Thr Ile Leu Arg Leu Ile
    2330                2335                2340 ttt tca gtt ggg ttg cag ccc aca ctg ttt ctg ctg gga gct ttc aat      7408
Phe Ser Val Gly Leu Gln Pro Thr Leu Phe Leu Leu Gly Ala Phe Asn
2345                2350                2355                2360 gtc tgc aat aaa atc atc ttc ctg atg agc ttt gtg ggc aac tgt ggg      7456
Val Cys Asn Lys Ile Ile Phe Leu Met Ser Phe Val Gly Asn Cys Gly
                2365                2370                2375 acc ttc acc aga ggc tac cgg gcc atg gtt ctg gat gtg gag ttc ctc      7504
Thr Phe Thr Arg Gly Tyr Arg Ala Met Val Leu Asp Val Glu Phe Leu
            2380                2385                2390 tat cat ttg ctg tat cta ctc atc tgt gcc atg ggc ctc ttc gta cat      7552
Tyr His Leu Leu Tyr Leu Leu Ile Cys Ala Met Gly Leu Phe Val His
        2395                2400                2405 gag ttc ttc tat agc ttg ctg ctt ttt gat tta gtg tac aga gag gag      7600
Glu Phe Phe Tyr Ser Leu Leu Leu Phe Asp Leu Val Tyr Arg Glu Glu
    2410                2415                2420 act ttg ctt aat gtc att aaa agt gtc acc cgc aat gga cgg tcc atc      7648
Thr Leu Leu Asn Val Ile Lys Ser Val Thr Arg Asn Gly Arg Ser Ile
2425                2430                2435                2440 atc ttg aca gcg gtc ctg gct ctg atc ctg gtt tac ctg ttc tca att      7696
Ile Leu Thr Ala Val Leu Ala Leu Ile Leu Val Tyr Leu Phe Ser Ile
                2445                2450                2455 gtg ggc tat ctg ttc ttc aag gat gac ttt atc ttg gaa gta gat agg      7744
Val Gly Tyr Leu Phe Phe Lys Asp Asp Phe Ile Leu Glu Val Asp Arg
            2460                2465                2470 ttg ccc aat gaa aca gct gtt cca gaa act ggc gag agt ttg gcc aac      7792
Leu Pro Asn Glu Thr Ala Val Pro Glu Thr Gly Glu Ser Leu Ala Asn
        2475                2480                2485 gat ttc ctg tac tct gat gtg tgc agg gta gag acg ggg gag aac tgc      7840
Asp Phe Leu Tyr Ser Asp Val Cys Arg Val Glu Thr Gly Glu Asn Cys
    2490                2495                2500 acc tct cct gca ccc aaa gaa gag ctg ctc cct gcc gaa gaa acg gaa      7888
Thr Ser Pro Ala Pro Lys Glu Glu Leu Leu Pro Ala Glu Glu Thr Glu
2505                2510                2515                2520 cag gat aag gaa cac acg tgt gag acc ctg ctc atg tgc atc gtc act      7936
Gln Asp Lys Glu His Thr Cys Glu Thr Leu Leu Met Cys Ile Val Thr
                2525                2530                2535 gtt ctg agt cac ggg ctg cgg agt ggg gga ggg gta gga gac gtg ctc      7984
Val Leu Ser His Gly Leu Arg Ser Gly Gly Gly Val Gly Asp Val Leu
```

-continued

| | |
|---|---|
| agg aag cca tcc aaa gag gag cct ctg ttt gct gca agg gtg atc tac<br>Arg Lys Pro Ser Lys Glu Glu Pro Leu Phe Ala Ala Arg Val Ile Tyr<br>        2555                      2560                        2565 | 8032 |
| gac ctc ctc ttc ttc ttc atg gtc atc atc atc gtc ctg aac ctg att<br>Asp Leu Leu Phe Phe Phe Met Val Ile Ile Ile Val Leu Asn Leu Ile<br>   2570                      2575                      2580 | 8080 |
| ttc ggg gtc atc atc gac acc ttt gct gac ctg agg agt gag aag caa<br>Phe Gly Val Ile Ile Asp Thr Phe Ala Asp Leu Arg Ser Glu Lys Gln<br>2585                     2590                      2595                      2600 | 8128 |
| aag aag gag gag atc tta aaa acc acg tgc ttc atc tgc ggc ttg gaa<br>Lys Lys Glu Glu Ile Leu Lys Thr Thr Cys Phe Ile Cys Gly Leu Glu<br>        2605                      2610                      2615 | 8176 |
| agg gac aag ttt gac aat aag act gtc acc ttt gaa gag cac atc aag<br>Arg Asp Lys Phe Asp Asn Lys Thr Val Thr Phe Glu Glu His Ile Lys<br>    2620                      2625                      2630 | 8224 |
| gaa gaa cac aac atg tgg cac tat ctg tgc ttc atc gtg ctg gtg aaa<br>Glu Glu His Asn Met Trp His Tyr Leu Cys Phe Ile Val Leu Val Lys<br>        2635                      2640                      2645 | 8272 |
| gtg aag gac tcc aca gag tac acc ggg cct gag agt tac gtg gca gag<br>Val Lys Asp Ser Thr Glu Tyr Thr Gly Pro Glu Ser Tyr Val Ala Glu<br>   2650                      2655                      2660 | 8320 |
| atc atc agg gaa aga aac ctt gat tgg ttc ctc aga atg aga gcc atg<br>Met Ile Arg Glu Arg Asn Leu Asp Trp Phe Leu Arg Met Arg Ala Met<br>2665                     2670                      2675                      2680 | 8368 |
| tcc ctg gtc agc agc gat tct gaa ggg gaa cag aac gag ctg agg aac<br>Ser Leu Val Ser Ser Asp Ser Glu Gly Glu Gln Asn Glu Leu Arg Asn<br>        2685                      2690                      2695 | 8416 |
| ctg cag gag aag ctg gag tct acc atg aag ctg gtc acc aat ctt tct<br>Leu Gln Glu Lys Leu Glu Ser Thr Met Lys Leu Val Thr Asn Leu Ser<br>    2700                      2705                      2710 | 8464 |
| ggc cag ctg tca gaa cta aag gac cag atg aca gaa cag agg aag cag<br>Gly Gln Leu Ser Glu Leu Lys Asp Gln Met Thr Glu Gln Arg Lys Gln<br>        2715                      2720                      2725 | 8512 |
| aaa caa aga atc ggc ctt cta gga cat cct cct cac atg aat gtc aac<br>Lys Gln Arg Ile Gly Leu Leu Gly His Pro Pro His Met Asn Val Asn<br>   2730                      2735                      2740 | 8560 |
| cca cag cag ccg gcc taggcaaatg aggcagaggg actctgctca gccctctgta<br>Pro Gln Gln Pro Ala<br>2745 | 8615 |
| tatcactgtc agggtgggta cggctcattg gttctgattt gcccactaag ggtacatgtg | 8675 |
| cgcttagtac atttgtaaat actcagtttt gtattgtatg tatatgattg ctattctcag | 8735 |
| aggtttggac tttcgtattg taattagctc tgttggcatg gtgacttgtc actcctgcca | 8795 |
| aaaatattaa aaatgccttt tttggaagga ctacagaaag tacctgatttt gcacttgaac | 8855 |
| cagattatag atttaaaagt atatgacatg tattttgtat ttaaaactag aatagccagt | 8915 |
| atttatgttt tttataaaac tgtgcaatac aaattatgca atcaccataa ctttgtaact | 8975 |
| cctgagtgtc ctaagggagt acacatcttt gaagctgatt tgttgatact cgtgtaataa | 9035 |
| atggttaaat atcaaatgct gctgctgctg ccaaaattat attaatagcg agtttctggc | 9095 |
| ccctgggcaa ttttgtacct tgtaattatc ctatggtgat gctgtttctc gttgctaatg | 9155 |
| gcattagtgc ccctgtatcc tagtgataac tccaggtctg tgaaccattc aaacagcatt | 9215 |
| cattttgaga aaagcaactt tagtttcaag gataatttta agcttcaaaa ttaatcatttt | 9275 |
| aaagtgtttc tttaagagag ccatgttaga ggctcacact ttagcttgaa aggagttgat | 9335 |
| gaattaattt tttaaaggga acttttttaca tgacgtttgg aataacagca tattgctgac | 9395 |

-continued

```
cagtcagtgt catctcccgg gtgaattttg atgtcacgtt atagtcaaat gagttagctg    9455
atggtttcta gattttcttc ctctgaacca tgatgcagta ggtaagaagt tattatgcgt    9515
atatacatat atacattcat atacgacaaa gtaggagctg tccccttagg atgcatagct    9575
gcccctaggg tacgtagctg aacactgaca atggcgttct tctgaaagag ccacgtttgg    9635
gttttatttc tttgtcacat gatttctttt ctggatgggc gcaaagtatc acaggaagtg    9695
ttttctctct gtcgccttgt tttgtacctg ggtctcgctt tactagaccg tctctgcaca    9755
aaagtttaaa aactgaaccg tatgcagagt tccgaagcaa gtcaagtttg taaatgcata    9815
cctaaaaata tttaataaac gatgcagaat cct                                  9848
```

<210> SEQ ID NO 4
<211> LENGTH: 2749
<212> TYPE: PRT
<213> ORGANISM: Mus musculus

<400> SEQUENCE: 4

```
Met Ser Asp Lys Met Ser Ser Phe Leu His Ile Gly Asp Ile Cys Ser
 1               5                  10                  15

Leu Tyr Ala Glu Gly Ser Thr Asn Gly Phe Ile Ser Thr Leu Gly Leu
            20                  25                  30

Val Asp Asp Arg Cys Val Val Gln Pro Glu Ala Gly Asp Leu Asn Asn
        35                  40                  45

Pro Pro Lys Lys Phe Arg Asp Cys Leu Phe Lys Leu Cys Pro Met Asn
    50                  55                  60

Arg Tyr Ser Ala Gln Lys Gln Phe Trp Lys Ala Lys Pro Gly Ala
65                  70                  75                  80

Asn Ser Thr Thr Asp Ala Val Leu Leu Asn Lys Leu His His Ala Ala
                85                  90                  95

Asp Leu Glu Lys Lys Gln Asn Glu Thr Glu Asn Arg Lys Leu Leu Gly
           100                 105                 110

Thr Val Ile Gln Tyr Gly Asn Val Ile Gln Leu Leu His Leu Lys Ser
       115                 120                 125

Asn Lys Tyr Leu Thr Val Asn Lys Arg Leu Pro Ala Leu Leu Glu Lys
   130                 135                 140

Asn Ala Met Arg Val Thr Leu Asp Glu Ala Gly Asn Glu Gly Ser Trp
145                 150                 155                 160

Phe Tyr Ile Gln Pro Phe Tyr Lys Leu Arg Ser Ile Gly Asp Ser Val
                165                 170                 175

Val Ile Gly Asp Lys Val Val Leu Asn Pro Val Asn Ala Gly Gln Pro
            180                 185                 190

Leu His Ala Ser Ser His Gln Leu Val Asp Asn Pro Gly Cys Asn Glu
        195                 200                 205

Val Asn Ser Val Asn Cys Asn Thr Ser Trp Lys Ile Val Leu Phe Met
    210                 215                 220

Lys Trp Ser Asp Asn Lys Asp Asp Ile Leu Lys Gly Gly Asp Val Val
225                 230                 235                 240

Arg Leu Phe His Ala Glu Gln Glu Lys Phe Leu Thr Cys Asp Glu His
                245                 250                 255

Arg Lys Lys Gln His Val Phe Leu Arg Thr Thr Gly Arg Gln Ser Ala
            260                 265                 270

Thr Ser Ala Thr Ser Ser Lys Ala Leu Trp Glu Val Glu Val Val Gln
        275                 280                 285
```

-continued

```
His Asp Pro Cys Arg Gly Gly Ala Gly Tyr Trp Asn Ser Leu Phe Arg
    290                 295                 300

Phe Lys His Leu Ala Thr Gly His Tyr Leu Ala Ala Glu Val Asp Pro
305                 310                 315                 320

Asp Phe Glu Glu Glu Cys Leu Glu Phe Gln Pro Ser Val Asp Pro Asp
                325                 330                 335

Gln Asp Ala Ser Arg Ser Arg Leu Arg Asn Ala Gln Glu Lys Met Val
            340                 345                 350

Tyr Ser Leu Val Ser Val Pro Glu Gly Asn Asp Ile Ser Ser Ile Phe
        355                 360                 365

Glu Leu Asp Pro Thr Thr Leu Arg Gly Gly Asp Ser Leu Val Pro Arg
    370                 375                 380

Asn Ser Tyr Val Arg Leu Arg His Leu Cys Thr Asn Thr Trp Val His
385                 390                 395                 400

Ser Thr Asn Ile Pro Ile Asp Lys Glu Glu Lys Pro Val Met Leu
                405                 410                 415

Lys Ile Gly Thr Ser Pro Leu Lys Glu Asp Lys Glu Ala Phe Ala Ile
            420                 425                 430

Val Pro Val Ser Pro Ala Glu Val Arg Asp Leu Asp Phe Ala Asn Asp
        435                 440                 445

Ala Ser Lys Val Leu Gly Ser Ile Ala Gly Lys Leu Glu Lys Gly Thr
    450                 455                 460

Ile Thr Gln Asn Glu Arg Arg Ser Val Thr Lys Leu Leu Glu Asp Leu
465                 470                 475                 480

Val Tyr Phe Val Thr Gly Gly Thr Asn Ser Gly Gln Asp Val Leu Glu
                485                 490                 495

Val Val Phe Ser Lys Pro Asn Arg Glu Arg Gln Lys Leu Met Arg Glu
            500                 505                 510

Gln Asn Ile Leu Lys Gln Ile Phe Lys Leu Leu Gln Ala Pro Phe Thr
        515                 520                 525

Asp Cys Gly Asp Gly Pro Met Leu Arg Leu Glu Glu Leu Gly Asp Gln
    530                 535                 540

Arg His Ala Pro Phe Arg His Ile Cys Arg Leu Cys Tyr Arg Val Leu
545                 550                 555                 560

Arg His Ser Gln Gln Asp Tyr Arg Lys Asn Gln Glu Tyr Ile Ala Lys
                565                 570                 575

Gln Phe Gly Phe Met Gln Lys Gln Ile Gly Tyr Asp Val Leu Ala Glu
            580                 585                 590

Asp Thr Ile Thr Ala Leu Leu His Asn Asn Arg Lys Leu Leu Glu Lys
        595                 600                 605

His Ile Thr Ala Ala Glu Ile Asp Thr Phe Val Ser Leu Val Arg Lys
    610                 615                 620

Asn Arg Glu Pro Arg Phe Leu Asp Tyr Leu Ser Asp Leu Cys Val Ser
625                 630                 635                 640

Met Asn Lys Ser Ile Pro Val Thr Gln Glu Leu Ile Cys Lys Ala Val
                645                 650                 655

Leu Asn Pro Thr Asn Ala Asp Ile Leu Ile Glu Thr Lys Leu Val Leu
            660                 665                 670

Ser Arg Phe Glu Phe Glu Gly Val Ser Thr Gly Glu Asn Ala Leu Glu
        675                 680                 685

Ala Gly Glu Asp Glu Glu Glu Val Trp Leu Phe Trp Arg Asp Ser Asn
    690                 695                 700

Lys Glu Ile Arg Ser Lys Ser Val Arg Glu Leu Ala Gln Asp Ala Lys
```

```
                705                    710                    715                    720
       Glu Gly Gln Lys Glu Asp Arg Asp Ile Leu Ser Tyr Tyr Arg Tyr Gln
                       725                    730                    735
       Leu Asn Leu Phe Ala Arg Met Cys Leu Asp Arg Gln Tyr Leu Ala Ile
                       740                    745                    750
       Asn Glu Ile Ser Gly Gln Leu Asp Val Asp Leu Ile Leu Arg Cys Met
                       755                    760                    765
       Ser Asp Glu Asn Leu Pro Tyr Asp Leu Arg Ala Ser Phe Cys Arg Leu
               770                    775                    780
       Met Leu His Met His Val Asp Arg Asp Pro Gln Glu Gln Val Thr Pro
       785                    790                    795                    800
       Val Lys Tyr Ala Arg Leu Trp Ser Glu Ile Pro Ser Glu Ile Ala Ile
                       805                    810                    815
       Asp Asp Tyr Asp Ser Ser Gly Thr Ser Lys Asp Glu Ile Lys Glu Arg
                       820                    825                    830
       Phe Ala Gln Thr Met Glu Phe Val Glu Glu Tyr Leu Arg Asp Val Val
                       835                    840                    845
       Cys Gln Arg Phe Pro Phe Ser Asp Lys Glu Lys Asn Lys Leu Thr Phe
               850                    855                    860
       Glu Val Val Asn Leu Ala Arg Asn Leu Ile Tyr Phe Gly Phe Tyr Asn
       865                    870                    875                    880
       Phe Ser Asp Leu Leu Arg Leu Thr Lys Ile Leu Leu Ala Ile Leu Asp
                       885                    890                    895
       Cys Val His Val Thr Thr Ile Phe Pro Ile Ser Lys Met Thr Lys Gly
                       900                    905                    910
       Glu Glu Asn Lys Gly Ser Asn Val Met Arg Ser Ile His Gly Val Gly
                       915                    920                    925
       Glu Leu Met Thr Gln Val Val Leu Arg Gly Gly Phe Leu Pro Met
               930                    935                    940
       Thr Pro Met Ala Ala Ala Pro Glu Gly Asn Val Lys Gln Ala Glu Pro
       945                    950                    955                    960
       Glu Lys Glu Asp Ile Met Val Met Asp Thr Lys Leu Lys Ile Ile Glu
                       965                    970                    975
       Ile Leu Gln Phe Ile Leu Asn Val Arg Leu Asp Tyr Arg Ile Ser Cys
                       980                    985                    990
       Leu Leu Cys Ile Phe Lys Arg Glu Phe Asp Glu Ser Asn Ser Gln Ser
                       995                    1000                   1005
       Ser Glu Thr Ser Ser Gly Asn Ser Ser Gln Glu Gly Pro Ser Asn Val
               1010                   1015                   1020
       Pro Gly Ala Leu Asp Phe Glu His Ile Glu Glu Gln Ala Glu Gly Ile
       1025                   1030                   1035                   1040
       Phe Gly Gly Ser Glu Glu Asn Thr Pro Leu Asp Leu Asp Asp His Gly
                       1045                   1050                   1055
       Gly Arg Thr Phe Leu Arg Val Leu Leu His Leu Thr Met His Asp Tyr
                       1060                   1065                   1070
       Pro Pro Leu Val Ser Gly Ala Leu Gln Leu Leu Phe Arg His Phe Ser
                       1075                   1080                   1085
       Gln Arg Gln Glu Val Leu Gln Ala Phe Lys Gln Val Gln Leu Leu Val
                       1090                   1095                   1100
       Thr Ser Gln Asp Val Asp Asn Tyr Lys Gln Ile Lys Gln Asp Leu Asp
       1105                   1110                   1115                   1120
       Gln Leu Arg Ser Ile Val Glu Lys Ser Glu Leu Trp Val Tyr Lys Gly
                       1125                   1130                   1135
```

-continued

Gln Gly Pro Asp Glu Pro Met Asp Gly Ala Ser Gly Glu Asn Glu His
            1140                 1145                 1150

Lys Lys Thr Glu Glu Gly Thr Ser Lys Pro Leu Lys His Glu Ser Thr
    1155                 1160                 1165

Ser Ser Tyr Asn Tyr Arg Val Val Lys Glu Ile Leu Ile Arg Leu Ser
    1170                 1175                 1180

Lys Leu Cys Val Gln Glu Ser Ala Ser Val Arg Lys Ser Arg Lys Gln
1185                 1190                 1195                 1200

Gln Gln Arg Leu Leu Arg Asn Met Gly Ala His Ala Val Val Leu Glu
            1205                 1210                 1215

Leu Leu Gln Ile Pro Tyr Glu Lys Ala Glu Asp Thr Lys Met Gln Glu
            1220                 1225                 1230

Ile Met Arg Leu Ala His Glu Phe Leu Gln Asn Phe Cys Ala Gly Asn
            1235                 1240                 1245

Gln Gln Asn Gln Ala Leu Leu His Lys His Ile Asn Leu Phe Leu Lys
            1250                 1255                 1260

Pro Gly Ile Leu Glu Ala Val Thr Met Gln His Ile Phe Met Asn Asn
1265                 1270                 1275                 1280

Phe Gln Leu Cys Ser Glu Ile Asn Glu Arg Val Val Gln His Phe Val
            1285                 1290                 1295

His Cys Ile Glu Thr His Gly Arg Asn Val Gln Tyr Ile Lys Phe Leu
            1300                 1305                 1310

Gln Thr Ile Val Lys Ala Glu Gly Lys Phe Ile Lys Lys Cys Gln Asp
            1315                 1320                 1325

Met Val Met Ala Glu Leu Val Asn Ser Gly Glu Asp Val Leu Val Phe
            1330                 1335                 1340

Tyr Asn Asp Arg Ala Ser Phe Gln Thr Leu Ile Gln Met Met Arg Ser
1345                 1350                 1355                 1360

Glu Arg Asp Arg Met Asp Glu Asn Ser Pro Leu Met Tyr His Ile His
            1365                 1370                 1375

Leu Val Glu Leu Leu Ala Val Cys Thr Glu Gly Lys Asn Val Tyr Thr
            1380                 1385                 1390

Glu Ile Lys Cys Asn Ser Leu Leu Pro Leu Asp Asp Ile Val Arg Val
            1395                 1400                 1405

Val Thr His Glu Asp Cys Ile Pro Glu Val Lys Ile Ala Tyr Ile Asn
    1410                 1415                 1420

Phe Leu Asn His Cys Tyr Val Asp Thr Val Glu Met Lys Glu Ile
1425                 1430                 1435                 1440

Tyr Thr Ser Asn His Met Trp Lys Leu Phe Glu Asn Phe Leu Val Asp
            1445                 1450                 1455

Ile Cys Arg Ala Cys Asn Asn Thr Ser Asp Arg Lys His Ala Asp Ser
            1460                 1465                 1470

Ile Leu Glu Lys Tyr Val Thr Glu Ile Val Met Ser Ile Val Thr Thr
            1475                 1480                 1485

Phe Phe Ser Ser Pro Phe Ser Asp Gln Ser Thr Thr Leu Gln Thr Arg
            1490                 1495                 1500

Gln Pro Val Phe Val Gln Leu Leu Gln Gly Val Phe Arg Val Tyr His
1505                 1510                 1515                 1520

Cys Asn Trp Leu Met Pro Ser Gln Lys Ala Ser Val Glu Ser Cys Ile
            1525                 1530                 1535

Arg Val Leu Ser Asp Val Ala Lys Ser Arg Ala Ile Ala Ile Pro Val
            1540                 1545                 1550

-continued

Asp Leu Asp Ser Gln Val Asn Asn Leu Phe Leu Lys Ser His Asn Ile
    1555                1560                1565

Val Gln Lys Thr Ala Leu Asn Trp Arg Leu Ser Ala Arg Asn Ala Ala
    1570                1575                1580

Arg Arg Asp Ser Val Leu Ala Ala Ser Arg Asp Tyr Arg Asn Ile Ile
1585                1590                1595                1600

Glu Arg Leu Gln Asp Ile Val Ser Ala Leu Glu Asp Arg Leu Arg Pro
            1605                1610                1615

Leu Val Gln Ala Glu Leu Ser Val Leu Val Asp Val Leu His Arg Pro
            1620                1625                1630

Glu Leu Leu Phe Pro Glu Asn Thr Asp Ala Arg Arg Lys Cys Glu Ser
            1635                1640                1645

Gly Gly Phe Ile Cys Lys Leu Ile Lys His Thr Lys Gln Leu Leu Glu
            1650                1655                1660

Glu Asn Glu Glu Lys Leu Cys Ile Lys Val Leu Gln Thr Leu Arg Glu
1665                1670                1675                1680

Met Met Thr Lys Asp Arg Gly Tyr Gly Glu Lys Gln Ile Ser Ile Asp
            1685                1690                1695

Glu Ser Glu Asn Ala Glu Leu Pro Gln Ala Pro Glu Ala Glu Asn Ser
            1700                1705                1710

Thr Glu Gln Glu Leu Glu Pro Ser Pro Pro Leu Arg Gln Leu Glu Asp
            1715                1720                1725

His Lys Arg Gly Glu Ala Leu Arg Gln Ile Leu Val Asn Arg Tyr Tyr
            1730                1735                1740

Gly Asn Ile Arg Pro Ser Gly Arg Arg Glu Ser Leu Thr Ser Phe Gly
1745                1750                1755                1760

Asn Gly Pro Leu Ser Pro Gly Gly Pro Ser Lys Pro Gly Gly Gly Gly
            1765                1770                1775

Gly Gly Pro Gly Ser Ser Ser Thr Ser Arg Gly Glu Met Ser Leu Ala
            1780                1785                1790

Glu Val Gln Cys His Leu Asp Lys Glu Gly Ala Ser Asn Leu Val Ile
            1795                1800                1805

Asp Leu Ile Met Asn Ala Ser Ser Asp Arg Val Phe His Glu Ser Ile
    1810                1815                1820

Leu Leu Ala Ile Ala Leu Leu Glu Gly Gly Asn Thr Thr Ile Gln His
1825                1830                1835                1840

Ser Phe Phe Cys Arg Leu Thr Glu Asp Lys Lys Ser Glu Lys Phe Phe
            1845                1850                1855

Lys Val Phe Tyr Asp Arg Met Lys Val Ala Gln Gln Glu Ile Lys Ala
            1860                1865                1870

Thr Val Thr Val Asn Thr Ser Asp Leu Gly Asn Lys Lys Lys Asp Asp
    1875                1880                1885

Glu Val Asp Arg Asp Ala Pro Ser Arg Lys Lys Ala Lys Glu Pro Thr
    1890                1895                1900

Thr Gln Ile Thr Glu Glu Val Arg Asp Gln Leu Leu Glu Ala Ser Ala
1905                1910                1915                1920

Ala Thr Arg Lys Ala Phe Thr Thr Phe Arg Arg Glu Ala Asp Pro Asp
            1925                1930                1935

Asp His Tyr Gln Ser Gly Glu Gly Thr Gln Ala Thr Thr Asp Lys Ala
            1940                1945                1950

Lys Asp Asp Leu Glu Met Ser Ala Val Ile Thr Ile Met Gln Pro Ile
    1955                1960                1965

Leu Arg Phe Leu Gln Leu Leu Cys Glu Asn His Asn Arg Asp Leu Gln

-continued

```
             1970            1975            1980
Asn Phe Leu Arg Cys Gln Asn Asn Lys Thr Asn Tyr Asn Leu Val Cys
1985            1990            1995            2000
Glu Thr Leu Gln Phe Leu Asp Cys Ile Cys Gly Ser Thr Thr Gly Gly
                2005            2010            2015
Leu Gly Leu Leu Gly Leu Tyr Ile Asn Glu Lys Asn Val Ala Leu Ile
            2020            2025            2030
Asn Gln Thr Leu Glu Ser Leu Thr Glu Tyr Cys Gln Gly Pro Cys His
            2035            2040            2045
Glu Asn Gln Asn Cys Ile Ala Thr His Glu Ser Asn Gly Ile Asp Ile
2050            2055            2060
Ile Thr Ala Leu Ile Leu Asn Asp Ile Asn Pro Leu Gly Lys Lys Arg
2065            2070            2075            2080
Met Asp Leu Val Leu Glu Leu Lys Asn Asn Ala Ser Lys Leu Leu Leu
                2085            2090            2095
Ala Ile Met Glu Ser Arg His Asp Ser Glu Asn Ala Glu Arg Ile Leu
            2100            2105            2110
Tyr Asn Met Arg Pro Lys Glu Leu Val Glu Val Ile Lys Lys Ala Tyr
            2115            2120            2125
Met Gln Gly Glu Val Glu Phe Glu Asp Gly Glu Asn Gly Glu Asp Gly
            2130            2135            2140
Ala Ala Ser Pro Arg Asn Val Gly His Asn Ile Tyr Ile Leu Ala His
2145            2150            2155            2160
Gln Leu Ala Arg His Asn Lys Glu Leu Gln Thr Met Leu Lys Pro Gly
                2165            2170            2175
Gly Gln Val Asp Gly Asp Glu Ala Leu Glu Phe Tyr Ala Lys His Thr
            2180            2185            2190
Ala Gln Ile Glu Ile Val Arg Leu Asp Arg Thr Met Glu Gln Ile Val
            2195            2200            2205
Phe Pro Val Pro Ser Ile Cys Glu Phe Leu Thr Lys Glu Ser Lys Leu
            2210            2215            2220
Arg Ile Tyr Tyr Thr Thr Glu Arg Asp Glu Gln Gly Ser Lys Ile Asn
2225            2230            2235            2240
Asp Phe Phe Leu Arg Ser Glu Asp Leu Phe Asn Glu Met Asn Trp Gln
                2245            2250            2255
Lys Lys Leu Arg Ala Gln Pro Val Leu Tyr Trp Cys Ala Arg Asn Met
                2260            2265            2270
Ser Phe Trp Ser Ser Ile Ser Phe Asn Leu Ala Val Leu Met Asn Leu
            2275            2280            2285
Leu Val Ala Phe Phe Tyr Pro Phe Lys Gly Val Arg Gly Gly Thr Leu
            2290            2295            2300
Glu Pro His Trp Ser Gly Leu Leu Trp Thr Ala Met Leu Ile Ser Leu
2305            2310            2315            2320
Ala Ile Val Ile Ala Leu Pro Lys Pro His Gly Ile Arg Ala Leu Ile
                2325            2330            2335
Ala Ser Thr Ile Leu Arg Leu Ile Phe Ser Val Gly Leu Gln Pro Thr
                2340            2345            2350
Leu Phe Leu Leu Gly Ala Phe Asn Val Cys Asn Lys Ile Ile Phe Leu
            2355            2360            2365
Met Ser Phe Val Gly Asn Cys Gly Thr Phe Thr Arg Gly Tyr Arg Ala
            2370            2375            2380
Met Val Leu Asp Val Glu Phe Leu Tyr His Leu Leu Tyr Leu Leu Ile
2385            2390            2395            2400
```

-continued

```
Cys Ala Met Gly Leu Phe Val His Glu Phe Phe Tyr Ser Leu Leu Leu
            2405                2410                2415
Phe Asp Leu Val Tyr Arg Glu Glu Thr Leu Leu Asn Val Ile Lys Ser
            2420                2425                2430
Val Thr Arg Asn Gly Arg Ser Ile Ile Leu Thr Ala Val Leu Ala Leu
            2435                2440                2445
Ile Leu Val Tyr Leu Phe Ser Ile Val Gly Tyr Leu Phe Phe Lys Asp
        2450                2455                2460
Asp Phe Ile Leu Glu Val Asp Arg Leu Pro Asn Glu Thr Ala Val Pro
2465                2470                2475                2480
Glu Thr Gly Glu Ser Leu Ala Asn Asp Phe Leu Tyr Ser Asp Val Cys
            2485                2490                2495
Arg Val Glu Thr Gly Glu Asn Cys Thr Ser Pro Ala Pro Lys Glu Glu
            2500                2505                2510
Leu Leu Pro Ala Glu Glu Thr Glu Gln Asp Lys Glu His Thr Cys Glu
            2515                2520                2525
Thr Leu Leu Met Cys Ile Val Thr Val Leu Ser His Gly Leu Arg Ser
            2530                2535                2540
Gly Gly Gly Val Gly Asp Val Leu Arg Lys Pro Ser Lys Glu Glu Pro
2545                2550                2555                2560
Leu Phe Ala Ala Arg Val Ile Tyr Asp Leu Leu Phe Phe Phe Met Val
            2565                2570                2575
Ile Ile Ile Val Leu Asn Leu Ile Phe Gly Val Ile Ile Asp Thr Phe
            2580                2585                2590
Ala Asp Leu Arg Ser Glu Lys Gln Lys Lys Glu Glu Ile Leu Lys Thr
            2595                2600                2605
Thr Cys Phe Ile Cys Gly Leu Glu Arg Asp Lys Phe Asp Asn Lys Thr
            2610                2615                2620
Val Thr Phe Glu Glu His Ile Lys Glu Glu His Asn Met Trp His Tyr
2625                2630                2635                2640
Leu Cys Phe Ile Val Leu Val Lys Val Lys Asp Ser Thr Glu Tyr Thr
            2645                2650                2655
Gly Pro Glu Ser Tyr Val Ala Glu Met Ile Arg Glu Arg Asn Leu Asp
            2660                2665                2670
Trp Phe Leu Arg Met Arg Ala Met Ser Leu Val Ser Ser Asp Ser Glu
            2675                2680                2685
Gly Glu Gln Asn Glu Leu Arg Asn Leu Gln Glu Lys Leu Glu Ser Thr
            2690                2695                2700
Met Lys Leu Val Thr Asn Leu Ser Gly Gln Leu Ser Glu Leu Lys Asp
2705                2710                2715                2720
Gln Met Thr Glu Gln Arg Lys Gln Lys Gln Arg Ile Gly Leu Leu Gly
            2725                2730                2735
His Pro Pro His Met Asn Val Asn Pro Gln Gln Pro Ala
            2740                2745

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
tgtcagacat atgcgtgttg gaa                                          23
```

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6
cgcgggatcc ttatttccgg ttgttgtgga gcaggg                        36

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
ccggaattct tatttccggt tgttgtggag caggg                         35

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
cgcggatcca tgaaatggag tgataacaaa gacgaca                       37

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
gagagcggca ggcactgatg aggg                                     24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
ccctcatcag tgcctgccgc tctc                                     24

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11
gctgaggttc aagacctgga ctttg                                    25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 12
aaagtccagg tcttgaacct cagc                                          24

<210> SEQ ID NO 13
<211> LENGTH: 1059
<212> TYPE: DNA
<213> ORGANISM: Mus musculus
<220> FEATURE:
<221> NAME/KEY: CDS
<222> LOCATION: (1)..(1059)

<400> SEQUENCE: 13

| tgg | agt | gat | aac | aaa | gac | gac | att | ctc | aaa | gga | ggt | gat | gtg | gtg | agg | 48 |
| Trp | Ser | Asp | Asn | Lys | Asp | Asp | Ile | Leu | Lys | Gly | Gly | Asp | Val | Val | Arg | |
| 1 | | | | 5 | | | | | 10 | | | | | 15 | | |

| ctc | ttc | cat | gcc | gag | caa | gag | aag | ttt | ctc | acc | tgt | gat | gag | cac | cgg | 96 |
| Leu | Phe | His | Ala | Glu | Gln | Glu | Lys | Phe | Leu | Thr | Cys | Asp | Glu | His | Arg | |
| | | | 20 | | | | | 25 | | | | | 30 | | | |

| aag | aag | cag | cat | gtg | ttc | ctg | agg | acc | acc | ggc | agg | cag | tca | gcc | acg | 144 |
| Lys | Lys | Gln | His | Val | Phe | Leu | Arg | Thr | Thr | Gly | Arg | Gln | Ser | Ala | Thr | |
| | 35 | | | | | 40 | | | | | 45 | | | | | |

| tcg | gcc | acc | agt | tct | aaa | gcc | ctg | tgg | gaa | gtg | gag | gta | gtc | cag | cac | 192 |
| Ser | Ala | Thr | Ser | Ser | Lys | Ala | Leu | Trp | Glu | Val | Glu | Val | Val | Gln | His | |
| 50 | | | | | 55 | | | | | 60 | | | | | | |

| gac | cca | tgt | cgg | ggt | gga | gct | ggg | tac | tgg | aat | agc | ctc | ttc | cgg | ttc | 240 |
| Asp | Pro | Cys | Arg | Gly | Gly | Ala | Gly | Tyr | Trp | Asn | Ser | Leu | Phe | Arg | Phe | |
| 65 | | | | 70 | | | | | 75 | | | | | 80 | | |

| aag | cac | ctg | gct | aca | ggg | cat | tac | ttg | gct | gca | gag | gta | gac | cct | gac | 288 |
| Lys | His | Leu | Ala | Thr | Gly | His | Tyr | Leu | Ala | Ala | Glu | Val | Asp | Pro | Asp | |
| | | | | 85 | | | | | 90 | | | | | 95 | | |

| ttt | gag | gaa | gaa | tgc | ctg | gag | ttt | cag | ccc | tca | gtg | gac | cct | gat | cag | 336 |
| Phe | Glu | Glu | Glu | Cys | Leu | Glu | Phe | Gln | Pro | Ser | Val | Asp | Pro | Asp | Gln | |
| | | | 100 | | | | | 105 | | | | | 110 | | | |

| gat | gca | tct | cgg | agt | agg | ttg | aga | aac | gcg | caa | gaa | aaa | atg | gta | tac | 384 |
| Asp | Ala | Ser | Arg | Ser | Arg | Leu | Arg | Asn | Ala | Gln | Glu | Lys | Met | Val | Tyr | |
| | 115 | | | | | 120 | | | | | 125 | | | | | |

| tct | ctg | gtc | tcc | gtg | cct | gaa | ggc | aac | gac | atc | tcc | tcc | atc | ttt | gag | 432 |
| Ser | Leu | Val | Ser | Val | Pro | Glu | Gly | Asn | Asp | Ile | Ser | Ser | Ile | Phe | Glu | |
| 130 | | | | | 135 | | | | | 140 | | | | | | |

| cta | gac | ccc | acg | act | ctg | cgt | gga | ggt | gac | agc | ctt | gtc | cca | agg | aac | 480 |
| Leu | Asp | Pro | Thr | Thr | Leu | Arg | Gly | Gly | Asp | Ser | Leu | Val | Pro | Arg | Asn | |
| 145 | | | | 150 | | | | | 155 | | | | | 160 | | |

| tcc | tat | gtc | cgt | ctc | aga | cac | ctg | tgc | acc | aac | acc | tgg | gta | cac | agc | 528 |
| Ser | Tyr | Val | Arg | Leu | Arg | His | Leu | Cys | Thr | Asn | Thr | Trp | Val | His | Ser | |
| | | | | 165 | | | | | 170 | | | | | 175 | | |

| aca | aac | atc | ccc | atc | gac | aag | gaa | gag | gag | aag | cct | gtg | atg | ctg | aaa | 576 |
| Thr | Asn | Ile | Pro | Ile | Asp | Lys | Glu | Glu | Glu | Lys | Pro | Val | Met | Leu | Lys | |
| | | | 180 | | | | | 185 | | | | | 190 | | | |

| att | ggt | acc | tct | ccc | ctg | aag | gag | gac | aag | gaa | gca | ttt | gcc | ata | gtt | 624 |
| Ile | Gly | Thr | Ser | Pro | Leu | Lys | Glu | Asp | Lys | Glu | Ala | Phe | Ala | Ile | Val | |
| | | 195 | | | | | 200 | | | | | 205 | | | | |

| cct | gtt | tcc | cct | gct | gag | gtt | cgg | gac | ctg | gac | ttt | gcc | aat | gat | gcc | 672 |
| Pro | Val | Ser | Pro | Ala | Glu | Val | Arg | Asp | Leu | Asp | Phe | Ala | Asn | Asp | Ala | |
| | 210 | | | | | 215 | | | | | 220 | | | | | |

```
agc aag gtg ctg ggc tcc atc gct ggg aag ttg gaa aag ggc acc atc      720
Ser Lys Val Leu Gly Ser Ile Ala Gly Lys Leu Glu Lys Gly Thr Ile
225                 230                 235                 240 acc cag aat gag aga agg tct gtc acg aag ctt ttg gaa gac ttg gtt      768
Thr Gln Asn Glu Arg Arg Ser Val Thr Lys Leu Leu Glu Asp Leu Val
                245                 250                 255 tac ttt gtc acg ggt gga act aac tct ggc caa gac gtg ctt gaa gtt      816
Tyr Phe Val Thr Gly Gly Thr Asn Ser Gly Gln Asp Val Leu Glu Val
            260                 265                 270 gtc ttc tct aag ccc aat cga gag cgg cag aag ctg atg agg gaa cag      864
Val Phe Ser Lys Pro Asn Arg Glu Arg Gln Lys Leu Met Arg Glu Gln
        275                 280                 285 aat att ctc aag cag atc ttc aag ctg ttg cag gcc ccc ttc acg gac      912
Asn Ile Leu Lys Gln Ile Phe Lys Leu Leu Gln Ala Pro Phe Thr Asp
    290                 295                 300 tgc ggg gat ggc ccg atg ctt cgg ctg gag gag ctg ggg gat cag cgc      960
Cys Gly Asp Gly Pro Met Leu Arg Leu Glu Glu Leu Gly Asp Gln Arg
305                 310                 315                 320 cat gct cct ttc aga cat att tgc cga ctc tgc tac agg gtc ctg cga     1008
His Ala Pro Phe Arg His Ile Cys Arg Leu Cys Tyr Arg Val Leu Arg
                325                 330                 335 cac tca cag caa gac tac agg aag aac cag gag tac ata gcc aag cag     1056
His Ser Gln Gln Asp Tyr Arg Lys Asn Gln Glu Tyr Ile Ala Lys Gln
            340                 345                 350
ttt                                                                 1059
Phe
```

<210> SEQ ID NO 14
<211> LENGTH: 353
<212> TYPE: PRT
<213> ORGANISM: Mus musculus

<400> SEQUENCE: 14

```
Trp Ser Asp Asn Lys Asp Ile Leu Lys Gly Gly Asp Val Val Arg
  1               5                  10                  15

Leu Phe His Ala Glu Gln Glu Lys Phe Leu Thr Cys Asp Glu His
                 20                  25                  30

Lys Lys Gln His Val Phe Leu Arg Thr Thr Gly Arg Gln Ser Ala Thr
         35                  40                  45

Ser Ala Thr Ser Ser Lys Ala Leu Trp Glu Val Glu Val Gln His
     50                  55                  60

Asp Pro Cys Arg Gly Gly Ala Gly Tyr Trp Asn Ser Leu Phe Arg Phe
 65                  70                  75                  80

Lys His Leu Ala Thr Gly His Tyr Leu Ala Ala Glu Val Asp Pro Asp
                 85                  90                  95

Phe Glu Glu Glu Cys Leu Glu Phe Gln Pro Ser Val Asp Pro Asp Gln
                100                 105                 110

Asp Ala Ser Arg Ser Arg Leu Arg Asn Ala Gln Glu Lys Met Val Tyr
            115                 120                 125

Ser Leu Val Ser Val Pro Glu Gly Asn Asp Ile Ser Ser Ile Phe Glu
        130                 135                 140

Leu Asp Pro Thr Thr Leu Arg Gly Gly Asp Ser Leu Val Pro Arg Asn
145                 150                 155                 160

Ser Tyr Val Arg Leu Arg His Leu Cys Thr Asn Thr Trp Val His Ser
                165                 170                 175

Thr Asn Ile Pro Ile Asp Lys Glu Glu Lys Pro Val Met Leu Lys
            180                 185                 190
```

```
                                        -continued

Ile Gly Thr Ser Pro Leu Lys Glu Asp Lys Glu Ala Phe Ala Ile Val
        195                 200                 205

Pro Val Ser Pro Ala Glu Val Arg Asp Leu Asp Phe Ala Asn Asp Ala
        210                 215                 220

Ser Lys Val Leu Gly Ser Ile Ala Gly Lys Leu Glu Lys Gly Thr Ile
225                 230                 235                 240

Thr Gln Asn Glu Arg Arg Ser Val Thr Lys Leu Leu Glu Asp Leu Val
                245                 250                 255

Tyr Phe Val Thr Gly Gly Thr Asn Ser Gly Gln Asp Val Leu Glu Val
                260                 265                 270

Val Phe Ser Lys Pro Asn Arg Glu Arg Gln Lys Leu Met Arg Glu Gln
        275                 280                 285

Asn Ile Leu Lys Gln Ile Phe Lys Leu Leu Gln Ala Pro Phe Thr Asp
        290                 295                 300

Cys Gly Asp Gly Pro Met Leu Arg Leu Glu Glu Leu Gly Asp Gln Arg
305                 310                 315                 320

His Ala Pro Phe Arg His Ile Cys Arg Leu Cys Tyr Arg Val Leu Arg
                325                 330                 335

His Ser Gln Gln Asp Tyr Arg Lys Asn Gln Glu Tyr Ile Ala Lys Gln
                340                 345                 350

Phe
```